(12) United States Patent
Basten et al.

(10) Patent No.: US 6,528,497 B1
(45) Date of Patent: Mar. 4, 2003

(54) SYNTHETIC POLYSACCHARIDES, THEIR METHOD OF PRODUCTION AND PHARMACEUTICAL COMPOSITIONS CONTAINING SAME

(75) Inventors: Johannes Basten, Afferden (NL); Cornelia Dreef-Tromp, Rauenstein (NL); Pierre Alexandre Driguez, Toulouse (FR); Philippe Duchaussoy, Toulouse (FR); Jean Marc Herbert, Tournefeuille (FR); Maurice Petitou, Paris cedex (FR); Constant Van Boeckel, Oss (NL)

(73) Assignees: Sanofi-Synthelabo, Paris (FR); Akzo Nobel N.V., Arhnem (NL)

( * ) Notice: Subject to any disclaimer, the term of this patent is extended or adjusted under 35 U.S.C. 154(b) by 0 days.

(21) Appl. No.: 09/600,506

(22) PCT Filed: Jan. 13, 1999

(86) PCT No.: PCT/FR99/00044

§ 371 (c)(1),
(2), (4) Date: Sep. 5, 2000

(87) PCT Pub. No.: WO99/36443

PCT Pub. Date: Jul. 22, 1999

(30) Foreign Application Priority Data

Jan. 19, 1998 (FR) .............................. 98 00515

(51) Int. Cl.[7] ...................... A61K 31/715; A61K 31/00; C07H 15/04; C08B 31/00
(52) U.S. Cl. .......................... 514/54; 514/25; 536/118; 536/123.1; 536/124; 536/122; 536/120; 536/121; 536/4.1
(58) Field of Search ............................. 536/118, 123.1, 536/124, 122, 120, 121, 4.1; 514/25, 54

(56) References Cited
FOREIGN PATENT DOCUMENTS
WO    WO 9747659     * 12/1997

* cited by examiner

Primary Examiner—Samuel Barts
Assistant Examiner—Michael G. Henry
(74) Attorney, Agent, or Firm—Paul E. Dupont; Michael D. Alexander

(57) ABSTRACT

Novel synthetic polysaccharides for use in the treatment of pathologies associated with a coagulation dysfunction.

24 Claims, No Drawings

SYNTHETIC POLYSACCHARIDES, THEIR METHOD OF PRODUCTION AND PHARMACEUTICAL COMPOSITIONS CONTAINING SAME

This is the National Phase Application of PCT/FR99/00044, filed Jan. 13, 1999.

The present invention relates to novel synthetic polysaccharides which have the anticoagulant and antithrombotic pharmacological activities of heparin.

Heparin belongs to the family of glycosaminoglycans (GAGs), which are heterogeneous natural sulphated polysaccharides.

Heparin preparations are mixtures of chains comprising a number of monosaccharide units ranging from 10 up to 100 or more. This molecular size heterogeneity is accompanied by a structural heterogeneity as regards not only the nature of the constituent monosaccharides but also the substituents they bear (L. Rodén in: "The Biochemistry of Glycoproteins and Glycosaminoglycans", edited by Lennarz W. J., Plenum Press, New York and London, 267–371, 1980).

Each family of natural GAGs generally has a range of pharmacological activities. All are combined in the preparations which can be obtained from natural products. Thus, for example, heparins and heparan sulphates have an antithrombotic activity which is associated with simultaneous action on several coagulation factors.

Heparin catalyses—in particular via antithrombin III (AT III)—the inhibition of two enzymes which are involved in the blood coagulation cascade, i.e. factor Xa and factor IIa (or thrombin). Preparations of low molecular weight heparins (LMWHs) contain chains formed of 4 to 30 monosaccharides and have the property of acting more selectively on factor Xa than on thrombin.

Certain synthetic oligosaccharides, in particular those described in EP 84999, have the property of selectively inhibiting, via antithrombin III, factor Xa without any activity on thrombin.

It is known that the inhibition of factor Xa requires the binding of heparin to AT III via the antithrombin binding domain (ABD), and that the inhibition of factor IIa (thrombin) requires binding to AT III, via the ABD, as well as to thrombin via a less well defined binding domain (TBD).

Synthetic oligosaccharides corresponding to the ABD of heparin are known and show antithrombotic activity in venous thrombosis. These compounds are described in EP 529,715 and EP 621,282 and in patent CA 2,040,905.

The efficacy of these oligosaccharides in the prevention of arterial thrombosis is nevertheless frustrated by their inability to inhibit thrombin.

A synthesis of heparin-type glycosaminoglycans capable of inhibiting thrombin via activation of AT III is described in patent application PCT/FR 97/01344.

That patent application describes novel biologically active polysaccharide derivatives. In particular, they are anticoagulant and antithrombotic. Furthermore, since these polysaccharides are obtained by synthesis, it is possible to selectively modify their structure, and in particular to remove unwanted sulphate substituents involved in interaction with certain basic proteins such as platelet factor 4 (PF4), which is released during the activation of the platelets, leading to considerable neutralization of heparin in the region of the clot. Thus, polysaccharides can be obtained which are powerful antithrombotic and anticoagulant agents and which, furthermore, can escape in vivo the action of proteins such as PF4, which neutralize the effect of heparin in particular on thrombin.

It has been shown in particular that these sulphated and alkylated polysaccharides can be powerful antithrombotic and anticoagulant agents depending on the arrangement of the alkyl groups and of the sulphate groups borne by the carbohydrate skeleton.

It has been found, more generally, that by making polysaccharide sequences, it is possible to accurately modify the GAG-type activities in order to obtain very active products which have the properties of heparin.

However, the use in human therapy of certain products described in patent application PCT/FR 97/01344 can prove to be difficult, in particular if these products have a long half-life. In the field of preventing or treating thrombosis with the above products, the fluidity of the blood must be re-established or maintained while at the same time avoiding the induction of a haemorrhage. The vital nature of the functions associated herewith is such that it is preferable to use, in order to obtain this equilibrium, only compounds which have a short half-life, which are easier to work with.

The reason for this is that it is well known that a haemorrhage can be triggered in a patient under treatment, due to any accidental cause whatsoever. It may also be necessary to perform surgery on a patient under antithrombotic treatment. For these various reasons also, it is preferred to use compounds with a short half-life.

The half-life of the synthetic polysaccharides of the invention was determined in rats, in which it was observed, unexpectedly, that it is influenced by the structure of the molecule and in particular of the ABD, of the TBD (thrombin binding domain) and of the spacer.

Thus, the present invention relates to novel synthetic polysaccharides, which are similar in structure to that of the compounds of patent application PCT/FR 97/01344, but which have specific properties. The reason for this is that these compounds unexpectedly have a half-life of removal, evaluated after intravenous administration to rats, by means of the anti-Xa activity, of less than one and a half hours.

These compounds are hexadecasaccharides comprising three distinct sequences: a sulphated pentasaccharide sequence DEFGH, a non-sulphated heptasaccharide sequence Z(MN)$_3$ and a sulphated tetrasaccharide sequence VWXY.

The compounds according to the present invention are synthetic polysaccharides in acidic form and the pharmaceutically acceptable salts thereof with pharmaceutically acceptable cations, the anionic form of which corresponds to one of the formulae (I), (II), (III), (IV) and (V) below:

Active structures of the invention

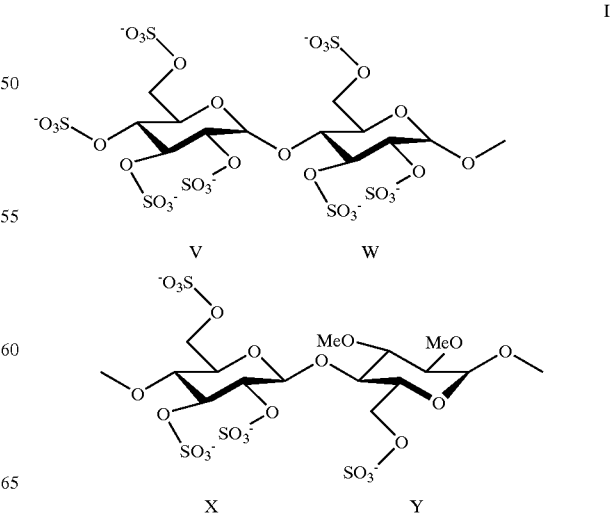

I

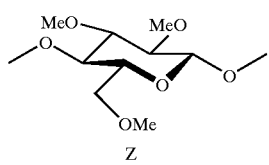
Z
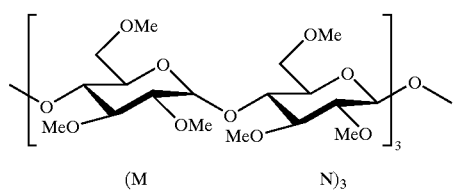
(M    N)₃
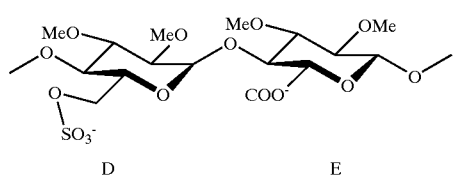
D    E
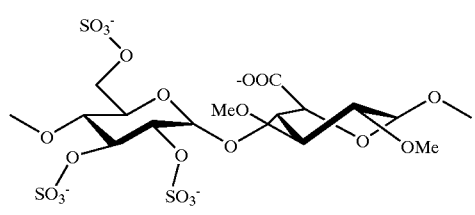
F    G
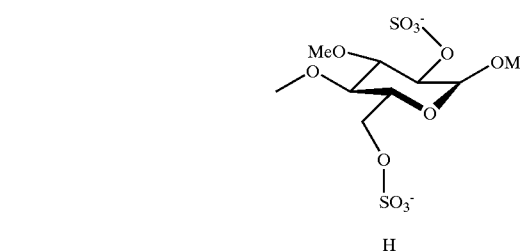
H
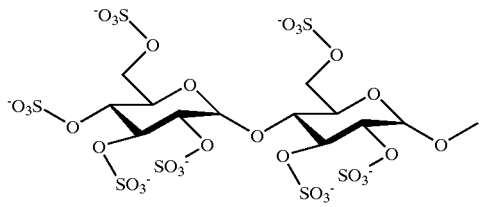
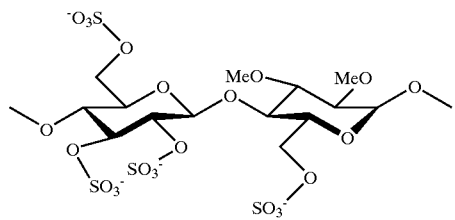
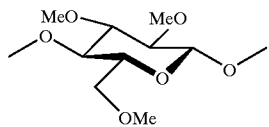
II
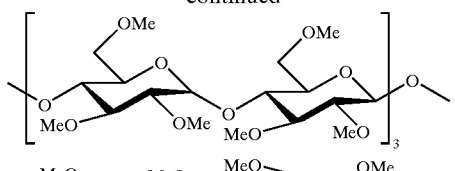
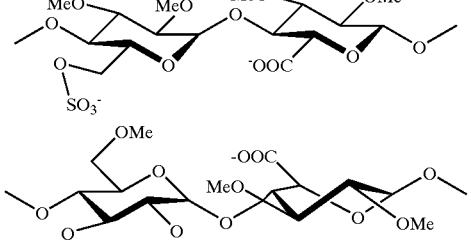
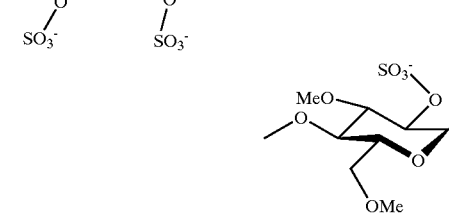
III
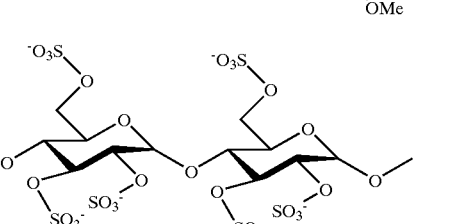
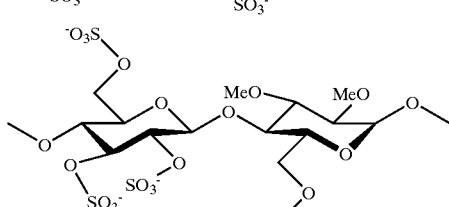
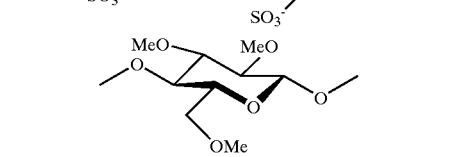
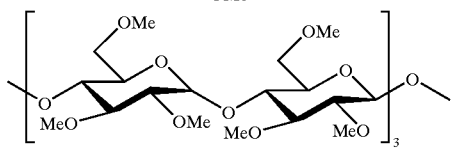
R¹ = CH₃
R² = SO₃⁻
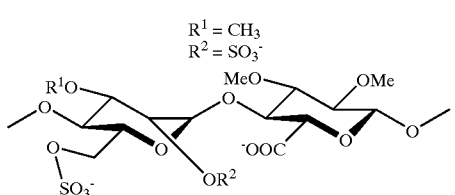
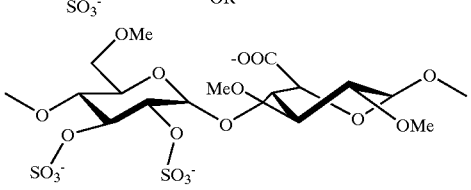

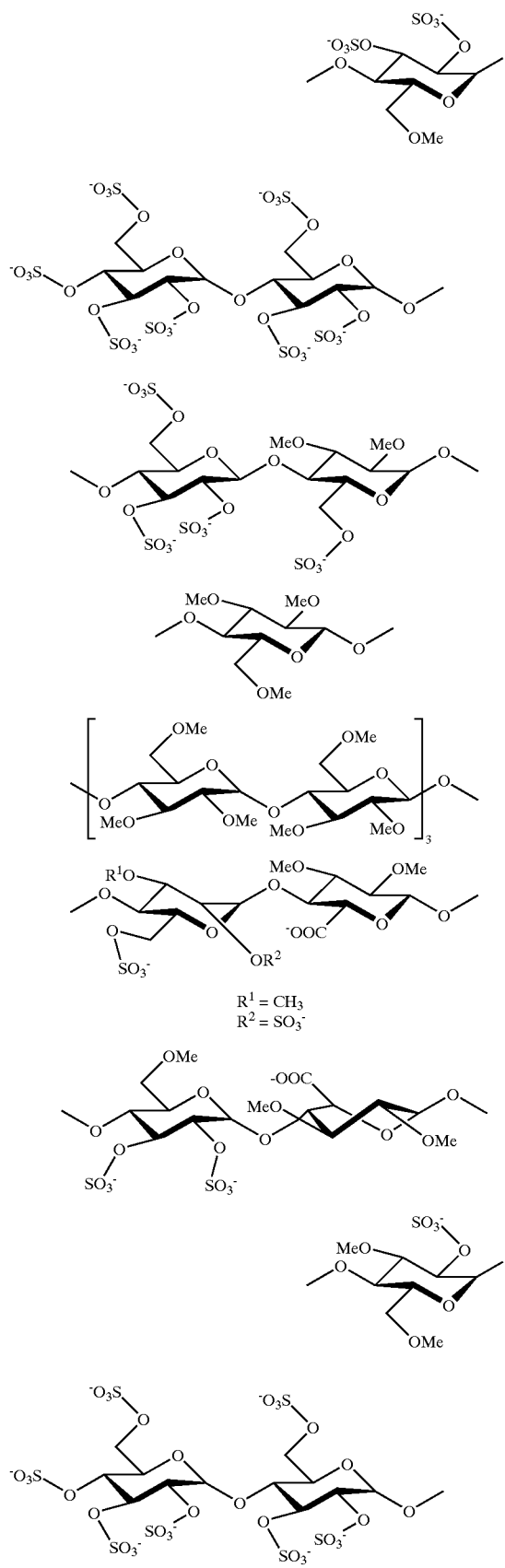
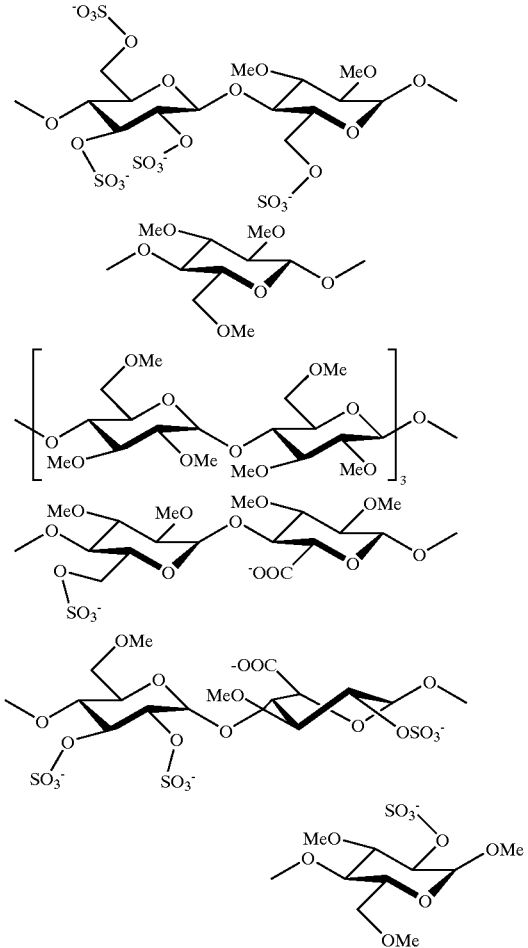

The invention encompasses the polysaccharides in their acidic form or in the form of any of the pharmaceutically acceptable salts thereof. In the acidic form, the —COO⁻ and —SO₃⁻ functions are in —COOH and —SO₃H form, respectively.

The expression "pharmaceutically acceptable salt of the polysaccharides of the invention" is intended to refer to a polysaccharide in which one or more of the —COO⁻ and/or —SO₃⁻ functions are ionically bonded to a pharmaceutically acceptable metal cation. The preferred salts according to the invention are those in which the cation is chosen from alkali metal cations, and even more preferably those in which the cation is Na⁺ or K⁺.

The present invention also relates to a process for preparing the polysaccharides of the invention.

In its principle, this process uses di- or oligosaccharide synthons prepared as reported previously in the literature. Reference will be made in particular to EP 300,099, EP 529,715, EP 621,282 and EP 649,854, as well as to C. van Boeckel, M. Petitou, Angew. Chem. Int. Ed. Engl., 1993, 32, 1671–1690. These synthons are then coupled together so as to give a fully protected precursor of a hexadecasaccharide according to the invention, which is then selectively deprotected and sulphated to give the hexadecasaccharide of the invention.

In the coupling reactions mentioned above, a "donor" di- or oligosaccharide, activated on its anomeric carbon, reacts with an "acceptor" di- or oligosaccharide, containing a free hydroxyl.

The hexadecasaccharides of the invention can be synthesized according to the following sequence of operations, which refer to the saccharide units as represented in formula (I) above.

A protected precursor of GH, pGH, which has an alcohol function in position 4', and a protected precursor of EF, pEF, whose anomeric carbon is activated, are first prepared. The intermediates pGH and pEF react together to give EFGH. Position 4 of the non-reductive end unit is then deprotected to give a precursor pEFGH.

In parallel, a precursor of the portion YZ(MN)$_3$D, whose anomeric carbon is activated, pYZ(MN)$_3$D, is prepared according to the same strategy.

The tetrasaccharide pEFGH then reacts with pYZ(MN)$_3$D to give YZ(MN)$_3$DEFGH. The non-reducing end unit is deprotected to give a precursor pYZ(MN)$_3$DEFGH.

A precursor of VWX, pVWX, is prepared in parallel.

Reaction between pVWX and pYZ(MN)$_3$DEFGH thus gives the direct precursor of the hexadecasaccharide, which is deprotected and sulphated to give the expected hexadecasaccharide.

It is obvious to those skilled in the art that several synthetic strategies are possible depending on the acceptors and donors chosen. It is possible, for example, to prepare a donor VWXYZ(MN)$_3$D and to couple it with EFGH in order to obtain a precursor of the desired hexadecasaccharide. Reference may be made, for example, to the above references and to Monosaccharides, Their chemistry and their roles in natural products, P. M. Collins and R. J. Ferrier, J. Wiley & Sons, 1995 and to G. J. Boons, Tetrahedron, 1996, 52, 1095–1121.

The compounds according to the invention have undergone biochemical and pharmacological studies which have shown that they moreover have the very advantageous properties of the products described in patent application PCT/FR 97/01344.

The compounds of the present invention which bind selectively to AT III with an affinity equal to or greater than that of heparin, have anticoagulant and antithrombotic properties which are superior to those of heparin.

The overall antithrombotic activity of the products of formula (I) to (V) has been evaluated intravenously or subcutaneously in rats, in a model of venous stasis and induction with thromboplastin, according to the method described by J. Reyers et al. in Thrombosis Research, 1980, 18, 669–674, as well as in a model of arterial thrombosis consisting of a shunt implanted between the carotid artery and the jugular vein in rats, as described by Umetsu et al. Thromb. Haemost., 1978, 39, 74–83. In these two experimental models, the ED$_{50}$ of the compounds of the invention is at least of the same order as or less than that of the other synthetic heparinoids already known (ED$_{50}$ of between 1 and 50 nmol/kg). The compounds of the invention thus have a particularly advantageous specificity of action and a particularly advantageous anticoagulant activity.

By virtue of their biochemical and pharmaceutical activity, the compounds of the present invention constitute very advantageous medicines. Their toxicity is entirely compatible with this use. They are also very stable and are thus particularly suitable for constituting the active principle of pharmaceutical specialities.

Furthermore, the compounds of the invention are not neutralized by high doses of cationic platelet proteins such as PF4, which are released on activation of the platelets during the process of thrombosis. The compounds of the invention are thus most particularly advantageous for treating and preventing thrombosis of either arterial or venous origin.

They can be used in various pathologies following a modification of the homeostasis of the coagulation system arising in particular during disorders of the cardiovascular and cerebrovascular systems, such as thromboembolic disorders associated with arteriosclerosis and with diabetes, such as unstable angina, strokes, restenosis after angioplasty, endarterectomy, the installation of endovascular prostheses; or thromboembolic disorders associated with rethrombosis after thrombolysis, infarction, dementia of ischaemic origin, with peripheral arterial diseases, with haemodialysis, with auricular fibrillations or during the use of aorto-coronary bridge vascular prostheses. This product can moreover be used for treating or preventing thromboembolic pathologies of venous origin, such as pulmonary embolisms. They can be used to prevent or treat thrombotic complications arising during surgery or in conjunction with other pathologies such as cancer and bacterial or viral infections. In the case of its use during the installation of prostheses, the compound of the present invention can cover the prostheses and thus make them compatible with the blood. In particular, they can be bound to intravascular prostheses (stents). In this case, they can optionally be chemically modified by introducing a suitable arm at the non-reductive or reductive end, as described according to EP 649,854.

The compounds of the present invention can also be used as adjuvants during endarterectomy carried out with porous balloons.

The compounds of the invention are very stable and are thus particularly suitable for constituting the active principle of medicines.

Thus, the compounds according to the invention can be used for the preparation of medicines intended to treat the above diseases.

According to another of its aspects, the subject of the present invention is thus a pharmaceutical composition containing, as active principle, a synthetic polysaccharide as defined above.

The invention preferably relates to pharmaceutical compositions containing, as active principle, a compound according to the invention in acidic form, or one of the pharmaceutically acceptable salts thereof, optionally in combination with one or more inert and appropriate excipients. In general, the polysaccharides of the invention can be used in the treatment of pathologies associated with a coagulation dysfunction.

In each dosage unit, the active principle is present in the amounts suited to the daily doses envisaged. In general, each dosage unit is appropriately adjusted according to the dosage and type of administration envisaged, for example tablets, gelatin capsules and the like, sachets, vials, syrups and the like, drops, transdermal or transmucous patches, such that such a dosage unit contains from 0.1 to 100 mg of active principle, preferably 0.5 to 50 mg.

The compounds according to the invention can also be used in combination with one or more other active principles which are useful for the desired therapy, such as, for example, antithrombotic agents, anticoagulants, anti-platelet-aggregating agents such as, for example, dipyridamole, aspirin, ticlopidine, clopidogrel or antagonists of the glycoprotein IIb/IIIa complex.

The pharmaceutical compositions are formulated for administration to mammals, including man, for the treatment of the abovementioned diseases.

The pharmaceutical compositions thus obtained are advantageously in various forms, such as, for example, injectable or drinkable solutions, sugar-coated tablets, ordinary tablets or gelatin capsules. Injectable solutions are the preferred pharmaceutical forms. The pharmaceutical compositions of the present invention are useful in particular for the preventive or curative treatment of vascular wall disorders, such as arteriosclerosis, the hypercoagulability states observed, for example, after surgery on tumours or after coagulation deregulation, induced by bacterial, viral or enzymatic activators. The dosage can vary within a wide range depending on the patient's age, weight and state of health, the nature and severity of the complaint, as well as on the route of administration. This dosage comprises the administration of one or more doses of about 0.1 mg to about 100 mg per day, preferably from about 0.5 to about 50 mg per day, intramuscularly or subcutaneously, in continuous administrations or at regular intervals.

The subject of the present invention is thus also pharmaceutical compositions which contain, as active principle, one of the above compounds optionally combined with another active principle. These compositions are made so as to be able to be administered via the digestive or parenteral route.

In the pharmaceutical compositions of the present invention for oral, sublingual, subcutaneous, intramuscular, intravenous, transdermal, transmucous, local or rectal administration, the active ingredient can be administered in unit forms of administration, mixed with standard pharmaceutical supports, to animals and to human beings. The appropriate unit forms of administration comprise oral forms such as tablets, gelatin capsules, powders, granules and oral suspensions or solutions, the sublingual and buccal forms of administration, the subcutaneous, intramuscular, intravenous, intranasal or intraocular forms of administration and the rectal forms of administration.

When a solid composition in tablet form is prepared, the main active ingredient is mixed with a pharmaceutical vehicle such as gelatin, starch, lactose, magnesium stearate, talc, gum arabic or the like. The tablets can be coated with sucrose or other suitable materials, or alternatively they can be treated such that they have sustained or delayed activity and such that they release a predetermined amount of active principle continuously.

A preparation in gelatin capsules is obtained by mixing the active ingredient with a diluent and by pouring the mixture obtained into soft or hard gelatin capsules.

The water-dispersible powders or granules can contain the active ingredient mixed with dispersion agents or wetting agents, or with suspension agents, such as polyvinylpyrrolidone, as well as with sweeteners or flavour enhancers.

For rectal administration, use is made of suppositories which are prepared with binders which melt at the rectal temperature, for example cocoa butter or polyethylene glycols.

For parenteral, intranasal or intraocular administration, aqueous suspensions, isotonic saline solutions or sterile injectable solutions which contain pharmacologically compatible dispersing agents and/or wetting agents, for example propylene glycol or butylene glycol, are used.

For transmucous administration, the active principle can be formulated in the presence of a promoter such as a bile salt, a hydrophilic polymer such as, for example, hydroxypropylcellulose, hydroxypropylmethylcellulose, hydroxyethylcellulose, ethylcellulose, carboxymethylcellulose, dextran, polyvinylpyrrolidone, pectins, starches, gelatin, casein, acrylic acids, acrylic esters and copolymers thereof, vinyl polymers or copolymers, vinyl alcohols, alkoxypolymers, polyethylene oxide polymers, polyethers or a mixture thereof.

The active principle can also be formulated in the form of microcapsules, optionally with one or more supports or additives.

The active principle can also be in the form of a complex with a cyclodextrin, for example α, β, or γ cyclodextrin, 2-hydroxypropyl-β-cyclodextrin or methyl-β-cyclodextrin.

The active principle can also be released by a balloon containing it or by an endovascular extender introduced into the blood vessels. The pharmacological efficacy of the active principle is thus not affected.

Subcutaneous administration is the preferred route.

The methods, the preparations and the schemes which follow illustrate the synthesis of the various intermediates which are useful for obtaining the polysaccharides according to the invention.

The following abbreviations are used: TBDMS: tert-butyldimethylsilyl; Lev: levulinoyl; Bn: benzyl; Bz: benzoyl; TLC: thin-layer chromatography; Olm: trichloroacetimidoyl; LSIMS: liquid secondary ion mass spectrometry; ESIMS: electron spray ionization mass spectrometry; TMS: trimethylsilyl; TSP: sodium trimethylsilyltetradeuteriopropionate; Tf: triflate; MS: molecular sieve; PMB: p-methoxybenzyl; MP: p-methoxyphenyl; TS: tosyl; ET: ethyl; Ph: phenyl; Me: methyl; Ac: acetyl.

Dowex®, Sephadex®, Chelex® and Toyopearl® are registered trade marks.

In the methods, the preparations and in the examples described below, general procedures regarding the catalytic coupling of the imidates, the cleavage of the levulinic esters, the catalytic coupling of the thioglycosides, the saponification, methylation and selective deprotection of the p-methoxybenzyl group, the deprotection and sulphation of the oligo- and polysaccharides by hydrogenolysis of the benzyl esters or ethers, the saponification of the esters or the sulphations can be carried out by applying the general methods below to the appropriate intermediates. Examples of the synthesis of the compounds of the invention are detailed for illustrative purposes hereinbelow.

SCHEME 1

Synthesis of the pentasaccharide 9

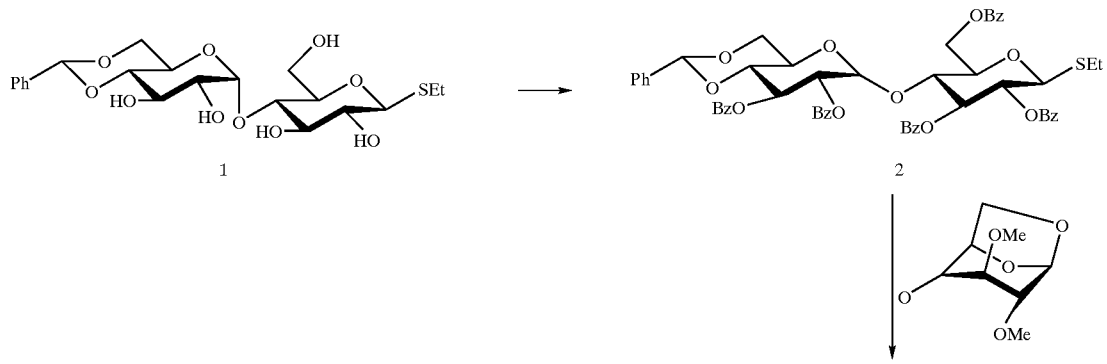

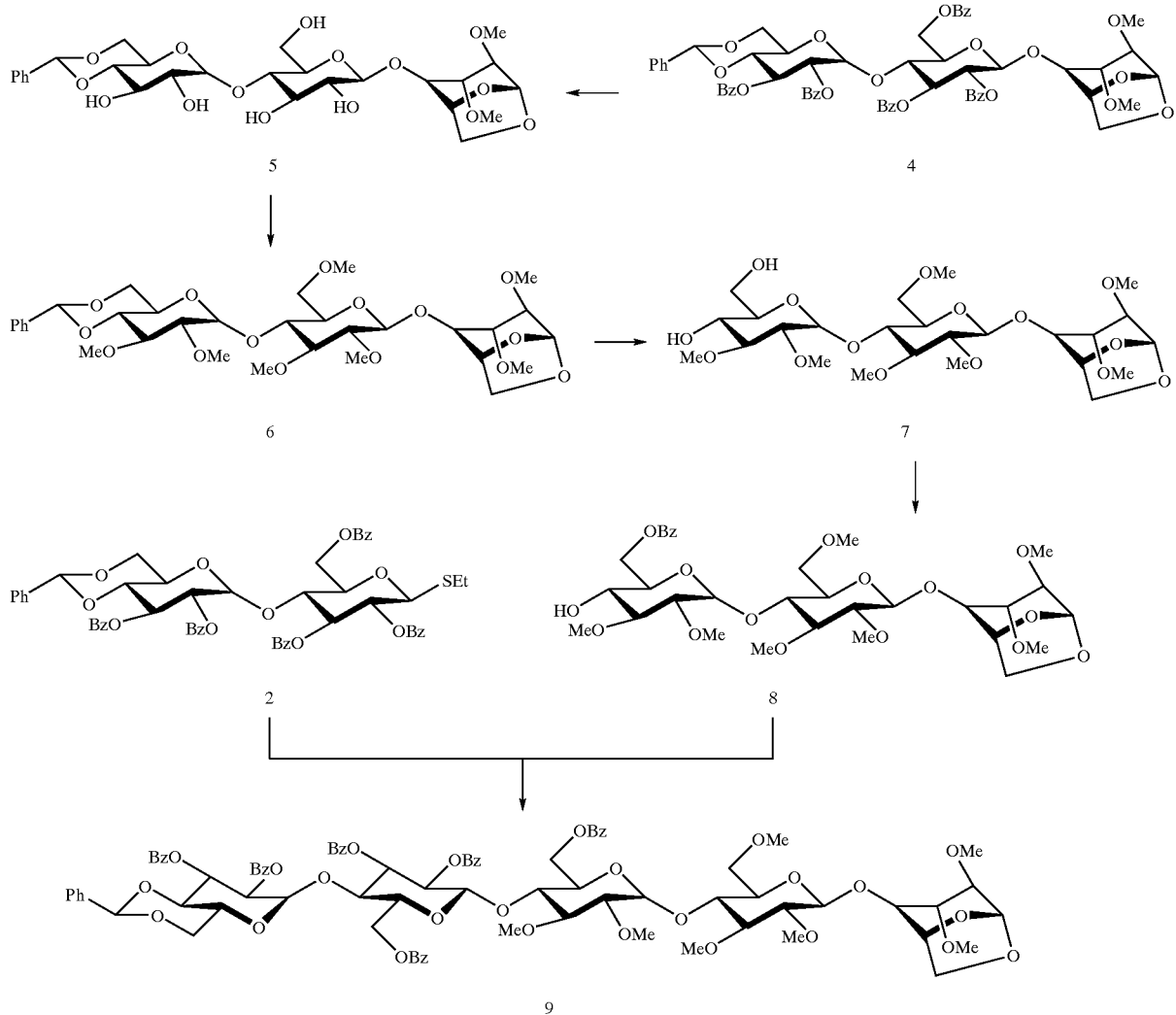

Preparation 1

Ethyl O-(2,3-di-O-benzoyl-4,6-O-benzylidene-α-D-glucopyranosyl)-(1→4)-2,3,6-tri-O-benzoyl-1-thio-β-D-glucopyranoside (2)

Benzoyl chloride (24.5 ml, 211 mmol) is added dropwise over 20 minutes to a cooled (0° C.) solution of compound 1 (16.7 g, 35.2 mmol) (J. Westman and M. Nilsson, J. Carbohydr. Chem., 1995, 14 (7), 949–960) in pyridine (202 ml). The reaction mixture is stirred for 20 hours at room temperature; TLC reveals an approximately 50% conversion. The mixture is diluted with water and dichloromethane. After extraction, the organic phase is washed with 10% sodium hydrogen carbonate solution and water, dried over magnesium sulphate and concentrated. The residue is retreated with benzoyl chloride according to the procedure described above. The crude product is purified by chromatography on a column of silica gel to give 22 g of compound 2.

TLC: Rf=0.80, silica gel, 9/1 v/v toluene/ethanol

Preparation 2

O-(2,3-Di-O-benzoyl-4,6-O-benzylidene-α-D-glucopyranosyl)-(1→4)-O-(2,3,6-tri-O-benzoyl-β-D-glucopyranosyl)-(1→4)-1,6-anhydro-2,3-di-O-methyl-β-D-glucopyranose (4)

A mixture of thioglycoside 2 (1.05 g, 1.05 mmol), compound 3 (200 mg, 1.05 mmol) (Jeanloz et al., J. Org. Chem. 1961, 26, 3939–3944) and powdered 4 Å molecular sieves (1.1 g) in toluene (18 ml) is stirred under a nitrogen atmosphere for 15 minutes. The mixture is then cooled to −20° C. and a freshly prepared solution of N-iodosuccinimide (1.11 mmol) and of trifluoromethanesulphonic acid (0.125 mmol) in 1/1 v/v dichloromethane/dioxane (6 ml) is introduced therein. After 10 minutes, the red reaction mixture is filtered, diluted with dichloromethane, extracted, washed successively with 10% sodium thiosulphate solution, 10% sodium hydrogen carbonate solution and water, dried over magnesium sulphate and then concentrated under vacuum. Purification of the residue is carried out by chromatography on a column of silica gel, to give 1.25 g of compound 4.

TLC: Rf=0.55, silica gel, 4/6 v/v heptane/ethyl acetate

Preparation 3

O-(4,6-O-Benzylidene-α-D-glucopyranosyl)-(1→4)-O-(β-D-glucopyranosyl)-(1→4)-1,6-anhydro-2,3-di-O-methyl-β-D-glucopyranose (5)

Potassium tert-butoxide (about 50 mg) is added to a solution of compound 4 (1.24 g, 1.11 mmol) in 1/1 v/v methanol/dioxane (7 ml). The mixture is stirred for one hour and a further 50 mg of potassium tert-butoxide are then added; the mixture is then stirred for a further 60 minutes. The reaction mixture is neutralized with a Dowex® 50WX8 H⁺ resin, filtered and concentrated under vacuum. After chromatography on a column of silica gel, 665 mg of compound 5 are isolated in the form of an oil.

TLC: Rf=0.50, silica gel, 85/15 v/v dichloromethane/methanol

Preparation 4

O-(4,6-O-Benzylidene-2,3-di-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (6)

Sodium hydride (387 mg, 9.65 mmol) is added, under a nitrogen atmosphere, to a cooled (5° C.) solution of compound 5 (660 mg, 1.1 mmol) in dry tetrahydrofuran (8 ml). Methyl iodide (0.51 ml, 8.22 mmol) is added dropwise and the mixture is stirred for 20 hours at room temperature. The excess sodium hydride is destroyed with methanol and the mixture is poured into 50 ml of ice-cold water. After extraction with ethyl acetate (3 times 20 ml), the organic phase is washed with sodium chloride solution, dried over magnesium sulphate and concentrated to give 690 mg of compound 6.

TLC: Rf=0.25, silica gel, 95/5 v/v dichloromethane/methanol

Preparation 5

O-(2,3-Di-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (7)

Compound 6 (690 mg, 1.03 mmol) is dissolved in 80% acetic acid (7.3 ml) and stirred for 20 hours at 40° C. The mixture is concentrated under vacuum and co-evaporated with toluene. Chromatography on a column of silica gel in 8/1/1 dichloromethane/ethyl acetate/methanol gives 569 mg of compound 7.

TLC: Rf=0.40, silica gel, 9/1 v/v dichloromethane/methanol

Preparation 6

O-(6-O-Benzoyl-2,3-di-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (8)

1-Benzyloxy-1H-benzotriazole (227 mg, 1.05 mmol) and triethylamine (1.15 mmol) are added to a solution of compound 7 (560 mg, 0.96 mmol) in dichloromethane and the mixture is then stirred for 20 hours at room temperature. The reaction mixture is diluted with dichloromethane and washed with 10% sodium hydrogen carbonate solution and water. The organic phase is dried over magnesium sulphate, filtered and evaporated to dryness. The product is purified by chromatography on a column of silica gel to give 600 mg of compound 8.

TLC: Rf=0.50, silica gel, 9/1 v/v dichloromethane/methanol

Preparation 7

O-(2,3-Di-O-benzoyl-4,6-O-benzylidene-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (9)

Compound 8 is converted into compound 9 according to the procedure described for the preparation of compound 4. The coupling reaction is carried out at 50° C.

TLC: Rf=0.50, silica gel, 2/8 v/v heptane/ethyl acetate

SCHEME 2

Synthesis of the heptasaccharide 14

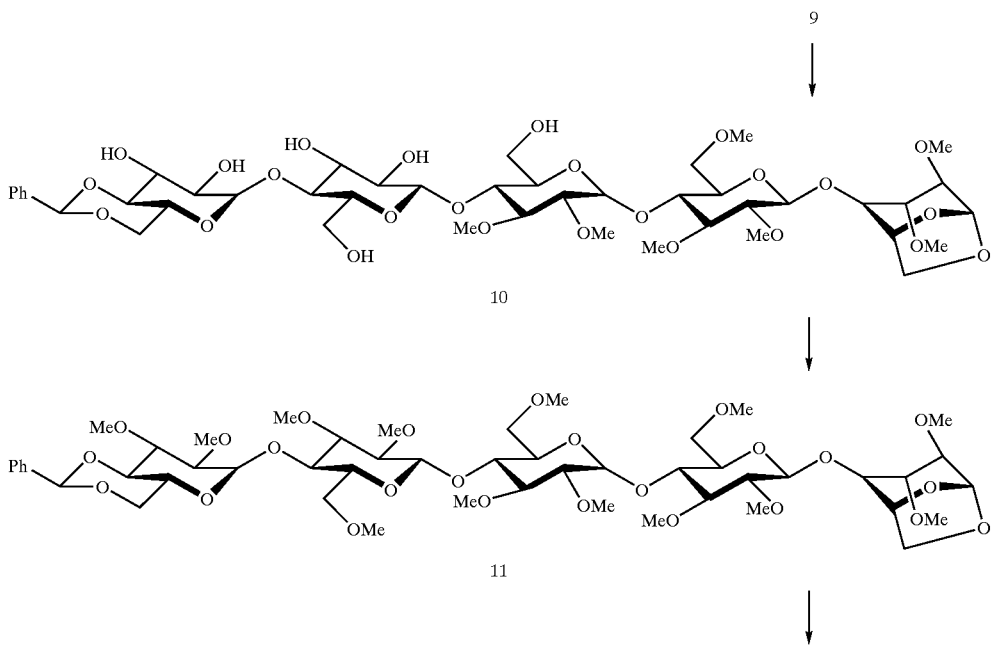

-continued

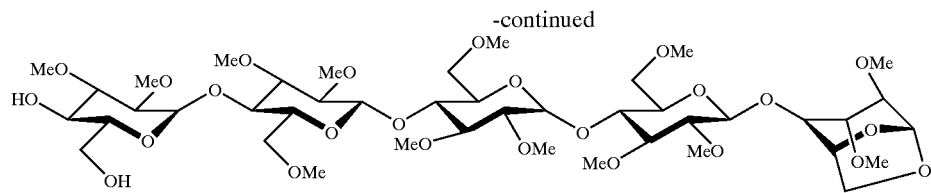

12

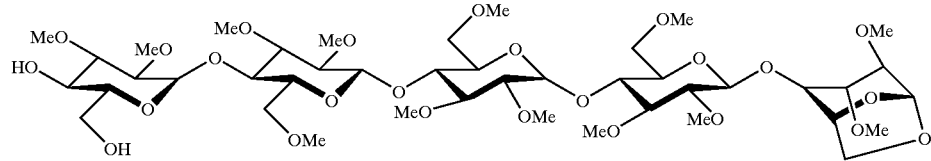

13

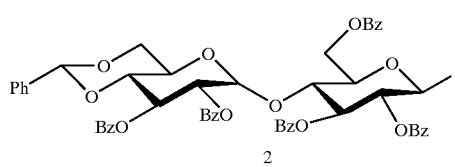

2

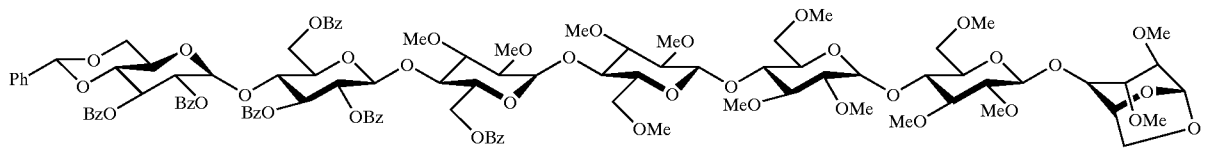

14

Preparation 8
O-(4,6-O-Benzylidene-α-D-glucopyranosyl)-(1→4)-O-(β-D-glucopyranosyl)-(1→4)-O-(2,3-di-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (10)

Compound 9 is converted into compound 10 according to the same procedure as that described for the preparation of compound 5.

TLC: Rf=0.35, silica gel, 9/1 v/v dichloromethane/methanol

Preparation 9
O-(4,6-O-Benzylidene-2,3-di-O-methyl-α-D-glucopyranosyl)-(1→4)-O-(2 3,6-tri-O-methyl-β-D-glucopyranosyl)-(1→4)-O-(2,3,6-tri-O-methyl-α-D-glucopyranosyl)-(1→4)-O-(2,3,6-tri-O-methyl-β-D-glucopyranosyl)-1,6-anhydro-2,3-di-O-methyl-β-D-glucopyranose (11)

Compound 10 is converted into compound 11 according to the same procedure as that described for the preparation of compound 6.

TLC: Rf=0.50, silica gel, 9/1 v/v dichloromethane/methanol

Preparation 10
O-(2,3-Di-O-methyl-α-D-glucopyranosyl)-(1→4)-O-(2,3,6-tri-O-methyl-β-D-glucopyranosyl)-(1→4)-O-(2,3,6-tri-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (12)

Compound 11 is converted into compound 12 according to the same procedure as that described for the preparation of compound 7.

TLC: Rf=0.35, silica gel, 9/1 v/v dichloromethane/methanol

Preparation 11
O-(6-O-Benzoyl-2,3-di-O-methyl-α-D-glucopyranosyl)-(1→4)-O-(2,3,6-tri-O-methyl-β-D-glucopyranosyl)-(1→4)-O-(2,3,6-tri-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (13)

Compound 12 is converted into compound 13 according to the same procedure as that described for the preparation of compound 8.

TLC: Rf=0.40, silica gel, 7.0/1.5/1.5 v/v/v toluene/ethyl acetate/ethanol

Preparation 12
O-(2,3-Di-O-benzoyl-4,6-O-benzylidene-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-O-(2,3,6-tri-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (14)

The coupling reaction of compound 13 with the disaccharide 2 is carried out according to the procedure described for the preparation of compound 9, to give compound 14.

TLC: Rf=0.40, silica gel, 7.0/1.5/1.5 v/v/v toluene/ethyl acetate/ethanol

SCHEME 3
Synthesis of the nonasaccharide 19
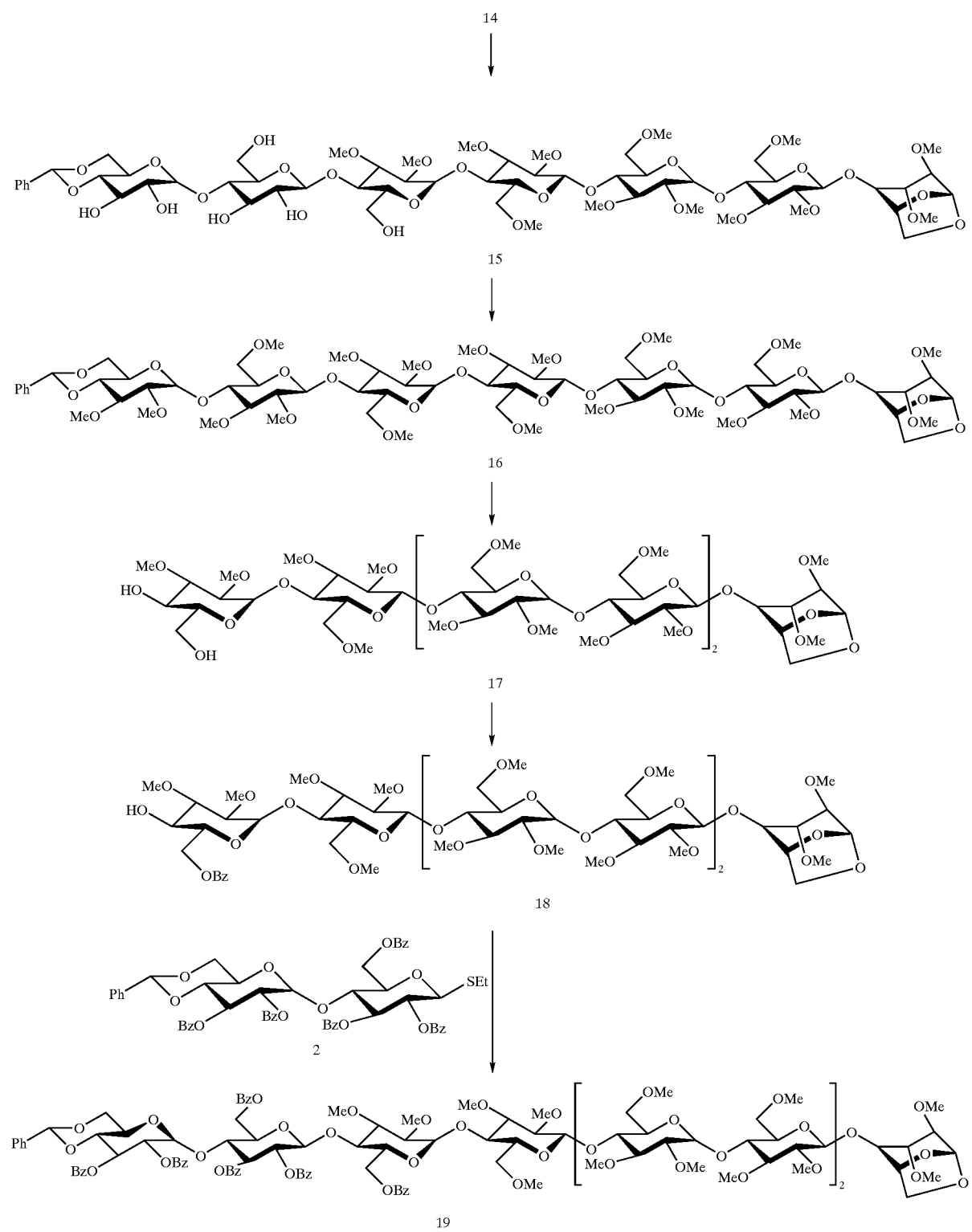

Preparation 13

O-(4,6-O-Benzylidene-α-D-glucopyranosyl)-(1→4)-O-(β-D-glucopyranosyl)-(1→4)-O-(2,3-di-O-methyl-α-D-glucopyranosyl)-(1→4)-O-(2,3,6-tri-O-methyl-β-D-glucopyranosyl)-(1→4)-O-(2,3,6-tri-O-methyl-α-D-glucopyranosyl)-(1→4)-O-(2,3,6-tri-O-methyl-β-D-glucopyranosyl)-(1→4)-1,6-anhydro-2,3-di-O-methyl-β-D-glucopyranose (15)

Compound 14 is converted into compound 15 according to the same procedure as that described for the preparation of compound 5.

TLC: Rf=0.60, silica gel, 9/1 v/v dichloromethane/methanol

Preparation 14

O-(4,6-O-Benzylidene-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_2$-1,6-anhydro-2,3-di-O-methyl-β-D-glucopyranose (16)

Compound 15 is converted into compound 16 according to the same procedure as that described for the preparation of compound 6.

TLC: Rf=0.70, silica gel, 9/1 v/v dichloromethane/methanol

Preparation 15

O-(2,3-Di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_2$-1,6-anhydro-2,3-di-O-methyl-β-D-glucopyranose (17)

A solution of compound 16 (5.05 g, 2.0 mmol) in 80% acetic acid (50 ml) is stirred for 20 hours at 40° C. The mixture is concentrated under vacuum and co-evaporated with toluene. The residue is dissolved in ethyl acetate and extracted with water. The aqueous phase is extracted with dichloromethane and the organic phase is dried over magnesium sulphate, filtered and evaporated to dryness to give 2.68 g of compound 17.

TLC: Rf=0.50, silica gel, 9/1 v/v dichloromethane/methanol

Preparation 16

O-(6-O-Benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_2$-1,6-anhydro-2,3-di-O-methyl-β-D-glucopyranose (18)

Compound 17 is converted into compound 18 according to the same procedure as that described for the preparation of compound 8.

TLC: Rf=0.80, silica gel, 7.0/1.5/1.5 v/v/v toluene/ethyl acetate/ethanol

Preparation 17

O-(2,3-Di-O-benzoyl-4,6-O-benzylidene-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_2$-1,6-anhydro-2,3-di-O-methyl-β-D-glucopyranose (19)

A mixture of the thioglycoside 2 (1.97 g, 2.0 mmol, 3.5 eq), of heptasaccharide 18 (0.86 g, 0.57 mmol) and of powdered 4 Å molecular sieves in toluene (22 ml) is stirred under a nitrogen atmosphere for 15 minutes. A freshly prepared solution containing N-iodosuccinimide (496 mg, 2.2 mmol) and trifluoro-methanesulphonic acid (0.808 mmol) in 1/1 v/v dichloromethane/dioxane (12 ml) is then added dropwise, at room temperature. After 10 minutes, the reaction mixture is filtered, diluted with dichloromethane, extracted, washed with 10% sodium thiosulphate solution and 10% sodium hydrogen carbonate solution, dried over magnesium sulphate and concentrated under vacuum. The crude product is purified by chromatography on a column of silica gel to give 1.09 g of compound 19.

TLC: Rf=0.80, silica gel, 6/2/2 v/v/v toluene/ethyl acetate/ethanol

SCHEME 4

Synthesis of the nonasaccharide 25

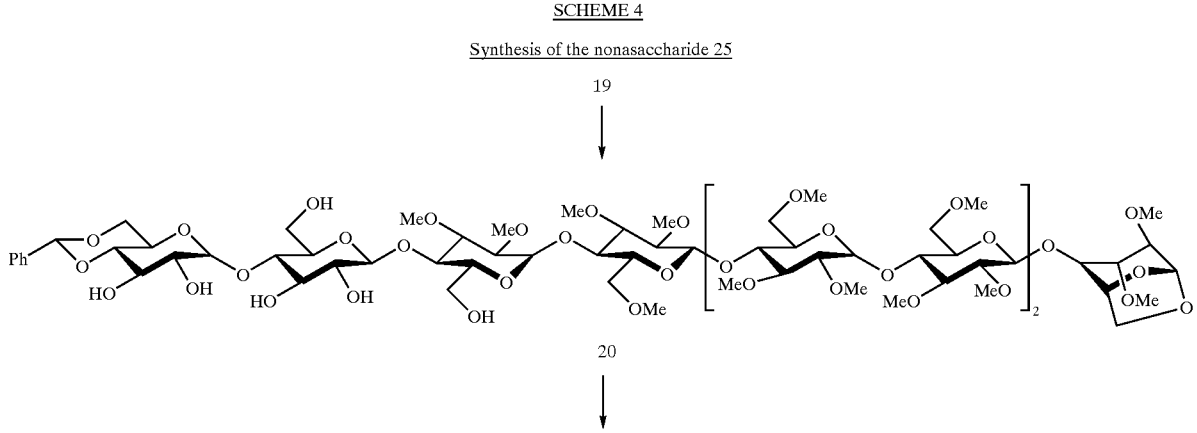

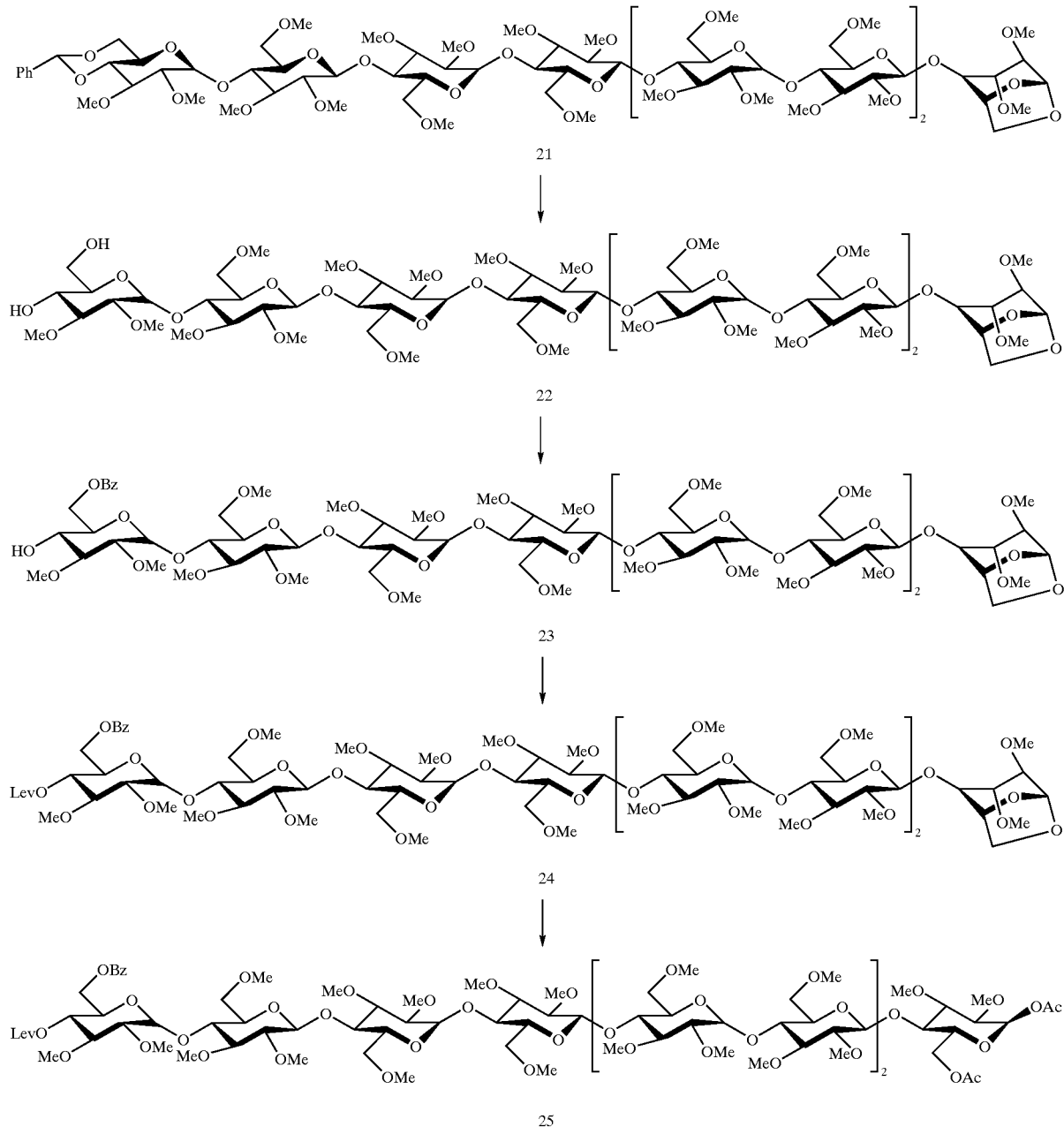

Preparation 18

O-(4,6-O-Benzylidene-α-D-glucopyranosyl)-(1→4)-O-(β-D-glucopyranosyl)-(1→4)-O-(2,3-di-O-methyl-α-D-glucopyranosyl)-(1→4)-O-(2,3,6-tri-O-methyl-β-D-glucopyranosyl)-[(1→4)-O-(2,3,6-tri-O-methyl-α-D-glucopyranosyl)-(1→4)-O-(2,3,6-tri-O-methyl-β-D-glucopyranosyl)]$_2$-(1→4)-1,6-anhydro-2,3-di-O-methyl-β-glucopyranose (20)

Compound 19 is converted into compound 20 according to the same procedure as that described for the preparation of compound 5.

TLC: Rf=0.25, silica gel, 5.0/2.5/2.5 v/v/v toluene/ethyl acetate/ethanol

Preparation 19

O-(4,6-O-Benzylidene-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-1,6-anhydro-2,3-di-O-methyl-β-D-glucopyranose (21)

Compound 20 is converted into compound 21 according to the same procedure as that described for the preparation of compound 6.

TLC: Rf=0.50, silica gel, 6/2/2 v/v/v toluene/ethyl acetate/ethanol

Preparation 20

O-(2,3-Di-O-methyl-α-D-glucopyranosyl)-(1→4)-
O-(2,3,6-tri-O-methyl-β-D-glucopyranosyl)-(1→4)-
[O-(2,3,6-tri-O-methyl-α-D-glucopyranosyl)-(1→4)-
O-(2,3,6-tri-O-methyl-β-D-glucopyranosyl)-(1→4)]₃-1,6-anhydro-2,3-di-O-methyl-β-D-glucopyranose (22)

Compound 21 is converted into compound 22 according to the same procedure as that described for the preparation of compound 7.

TLC: Rf=0.20, silica gel, 6/2/2 v/v/v toluene/ethyl acetate/ethanol

Preparation 21

O-(6-O-Benzoyl-2,3-di-O-methyl-α-D-glucopyranosyl)-(1→4)-O-(2,3,6-tri-O-methyl-β-D-glucopyranosyl)-(1→4)-[-O-(2,3,6-tri-O-methyl-α-D-glucopyranosyl)-(1→4)-O-(2,3,6-tri-O-methyl-β-D-glucopyranosyl)-(1→4)]₃-1,6-anhydro-2,3-di-O-methyl-β-D-glucopyranose (23)

Compound 22 is converted into compound 23 according to the same procedure as that described for the preparation of compound 8.

TLC: Rf=0.20, silica gel, 6/2/2 v/v/v toluene-ethyl acetate/ethanol in dioxane (1 ml). The reaction mixture is stirred for 3 hours at room temperature under a nitrogen atmosphere. Dichloromethane and water are then added and, after extraction, the organic phase is washed with water, dried over magnesium sulphate, filtered and concentrated. The crude product is purified by chromatography on a column of silica gel to give 312 mg of compound 24.

TLC: Rf=0.50, silica gel, 6/2/2 v/v/v toluene/ethyl acetate/ethanol

Preparation 23

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-di-O-acetyl-2,3-di-O-methyl-α,β-D-glucopyranose (25)

A solution of compound 24 (312 mg, 0.155 mmol) in a mixture of acetic anhydride (2.25 ml), acetic acid (50 µl) and trifluoroacetic acid (0.14 ml) is stirred for 4 hours at room temperature. After adding toluene (10 ml), the mixture is concentrated and co-evaporated with the toluene (3 times 10 ml). After chromatography on a column of silica gel, 324 mg of compound 25 are isolated.

TLC: Rf=0.65, silica gel, 6/2/2 v/v/v toluene/ethyl acetate/ethanol

SCHEME 5

Synthesis of the nonasaccharide 27

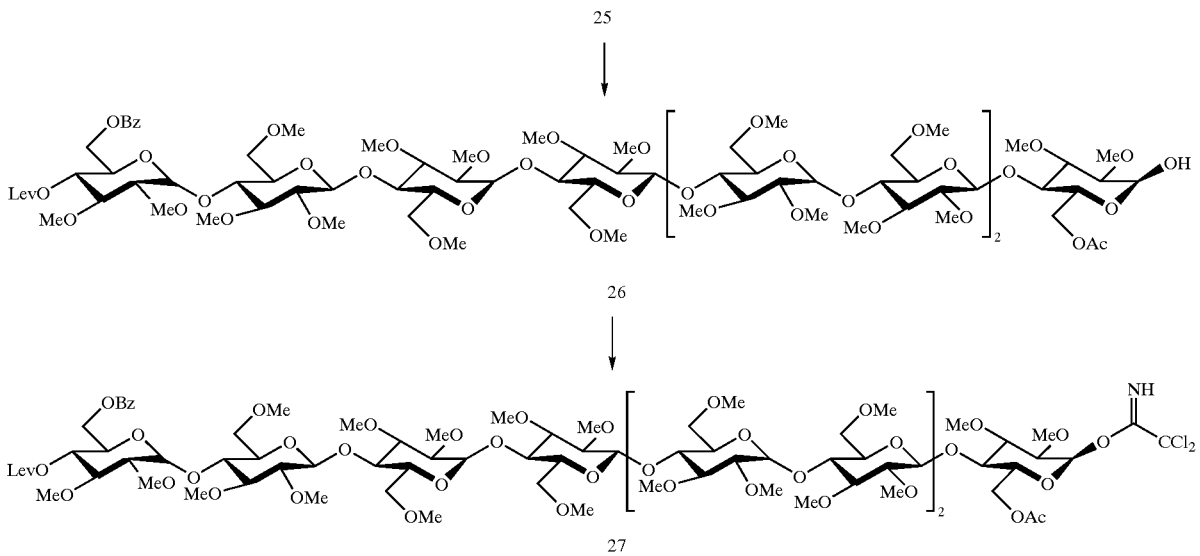

Preparation 22

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-anhydro-2,3-di-O-methyl-β-D-glucopyranose (24)

1-(3-Dimethylaminopropyl)-3-ethylcarbodiimide hydrochloride (48 mg, 0.25 mmol), levulinic acid (29 mg, 0.25 mmol) and dimethylaminopyridine (4 mg, 0.033 mmol) are added to a solution of compound 23 (320 mg, 0.167 mmol)

Preparation 24

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-6-O-acetyl-2,3-di-O-methyl-α,β-D-glucopyranose (26)

A solution of compound 25 (324 mg, 0.153 mmol) and of morpholine (22.3 µl, 0.256 mmol) in toluene (2 ml) is stirred for 4 hours at 35° C. Next, morpholine (22.3 µl) is again added and the reaction mixture is stirred for 20 hours at 35°

C. The mixture is cooled rapidly with water. After extraction with dichloromethane, the organic phase is successively washed with 0.1N hydrochloric acid and water, dried and evaporated to dryness. After chromatography on a column of silica gel, 280 mg of compound 26 are isolated.

TLC: Rf=0.45, silica gel, 6/2/2 v/v/v toluene/ethyl acetate/ethanol

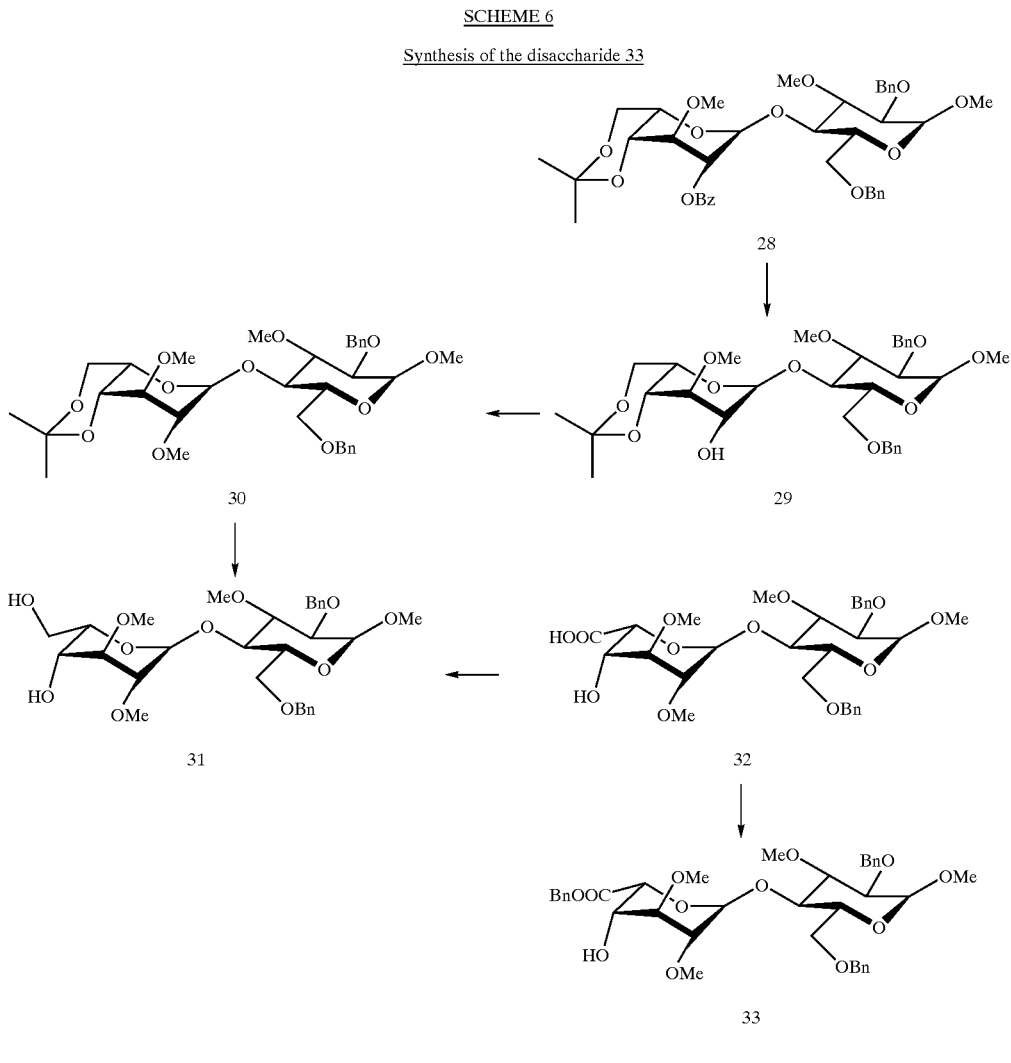

SCHEME 6
Synthesis of the disaccharide 33

Preparation

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-6-O-acetyl-2,3-di-O-methyl-α,β-D-glucopyranose trichloroacetimidate (27)

Trichloroacetonitrile (39 μl, 0.39 mmol) and caesium carbonate (4.7 mg) are added to a solution of compound 26 (138 mg, 0.066 mmol) in dichloromethane (1.5 ml). After stirring for 2 hours, the mixture is filtered, concentrated and the residue is chromatographed on a column of silica gel to give 152 mg of the imidate 27.

TLC: Rf=0.35, silica gel, 8/1/1 v/v/v toluene/ethyl acetate/ethanol

Preparation 26

Methyl-O-(4,6-O-isopropylidene-3-O-methyl-α-L-idopyranosyl-(1→4)-2,6-di-O-benzyl-3-O-methyl-α-D-glucopyranoside (29)

Compound 28 (2.5 g, 3.53 mmol) (M. Petitou et al., J. Med. Chem. 1997, 40, 1600) is treated as for the synthesis of 5, and, after chromatography on silica (2/1 cyclohexane/ethyl acetate), give 29 (2.1 g, 98%).

TLC: Rf=0.32, silica gel, 2/1 v/v cyclohexane/ethyl acetate

Preparation 27

Methyl-O-(4,6-O-isopropylidene-2,3-di-O-methyl-α-L-idopyranosyl-(1→4)-2,6-di-O-benzyl-3-O-methyl-α-D-glucopyranoside (30)

Compound 29 (2.0 g, 3.3 mmol) is treated as for the synthesis of compound 6, and, after chromatography on silica (5/1 cyclohexane/ethyl acetate), give compound 30 (1.83 g, 89%).

TLC: Rf=0.38, silica gel, 5/2 v/v cyclohexane/ethyl acetate

Preparation 28

Methyl-O-(2,3-di-O-methyl-α-L-idopyranosyl-(1→4)-2,6-di-O-benzyl-3-O-methyl-α-D-glucopyranoside (31)

Aqueous 70% trifluoroacetic acid solution (3.14 ml) is added to a solution of compound 30 (1.76 g, 2.84 mmol) in dichloromethane (16 ml). After 50 minutes, the reaction medium is diluted in dichloromethane and then washed with water until neutral. The organic phase is then dried (sodium sulphate), filtered and then concentrated. The residue is purified on silica to give compound 31 (1.45 g, 88%).

carbonate (0.67 g) and benzyl bromide (1.07 ml) are added and the mixture is stirred for 90 minutes. Ethyl acetate and water are added and, after extraction, the organic phase is concentrated. Purification by chromatography on a column of silica gel gives 0.99 g of compound 33.

TLC: Rf=0.58, silica gel, 1/4 v/v toluene/diethyl ether

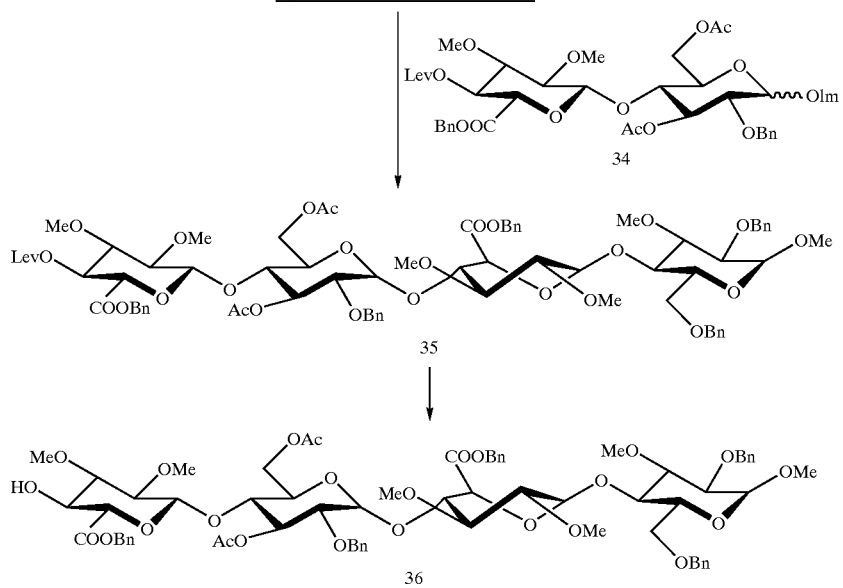

SCHEME 7
Synthesis of the tetrasaccharide 36

$[\alpha]^{20}_D$=+10 (c=1.0, dichloromethane).

Preparation 29

Methyl-O-(2,3-di-O-methyl-α-L-idopyranosyluronic acid)-(1→4)-2,6-di-O-benzyl-3-O-methyl-α-D-glucopyranoside (32)

2,2,6,6-Tetramethyl-1-piperidinyloxy (3.3 mg), a sodium hydrogen carbonate solution (4 ml), potassium bromide (22 mg) and tetrabutylammonium chloride (29 mg) are added to a solution of compound 31 (1.16 g) in dichloromethane (6 ml). The mixture is cooled to 0° C. and a mixture of saturated sodium chloride solution (4.4 ml), saturated sodium hydrogen carbonate solution (2.2 ml) and sodium hypochlorite (1.3 M, 5 ml) is added over 15 minutes. After stirring for 1 hour, the mixture is diluted with water and extracted (3 times) with dichloromethane. The organic phase is washed with aqueous sodium chloride solution, dried over magnesium sulphate, filtered and evaporated to dryness to give 1.34 g of the crude compound 32.

Rf=0.22, silica gel, 10/1 v/v dichloromethane/methanol.

Preparation 30

Methyl-O-(benzyl-2,3-di-O-methyl-α-L-idopyranosyluronate)-(1→4)-2,6-di-O-benzyl-3-O-methyl-α-D-glucopyranoside (33)

Compound 32 is dissolved in N,N-dimethylformamide (11 ml) under a nitrogen atmosphere. Potassium hydrogen

Preparation 31

Methyl-O-(benzyl-4-O-levulinoyl-2,3-di-O-methyl-β-D-glucopyranosyluronate-(1→4)-O-(3,6-di-O-acetyl-2-O-benzyl-α-D-glucopyranosyl)-(1→4)-O-(benzyl 2,3-di-O-methyl-α-L-idopyranosyluronate)-(1→4)-2,6-di-O-benzyl-3-O-methyl-α-D-glucopyranoside (35)

Compound 34 (274 mg, 0.31 mmol) (M. Petitou, et al., J.Med. Chem., 1997, 40, 1600) and compound 33 (200 mg, 0.29 mmol) in toluene (10 ml) are treated in the presence of a molecular sieve (220 mg), and at −20° C., with tert-butyldimethylsilyl trifluoromethanesulphonate (0.15 ml of a 1 molar solution in toluene). After stirring for 10 minutes, the reaction mixture is neutralized (NaHCO₃), filtered and concentrated. Chromatography on a column of silica gel gives compound 35 (334 mg, 80%).

$[\alpha]^{20}_D$=+31 (c=0.76, dichloromethane)

Preparation 32

Methyl-O-(benzyl 2,3-di-O-methyl-β-D-glucopyranosyl-uronate)-(1→4)-O-(3,6-di-O-acetyl-2-O-benzyl-α-D-glucopyranosyl)-(1→4)-O-(benzyl 2,3-di-O-methyl-α-L-idopyranosyluronate)-(1→4)-2,6-di-O-benzyl-3-O-methyl-α-D-glucopyranoside (36)

Compound 35 (308 mg, 0.22 mmol) is dissolved in a toluene/ethanol mixture (1/2, 43 ml) and hydrazine acetate (101 mg, 5 eq) is then added. After stirring for 45 minutes, the mixture is concentrated and then purified on a column of silica to give compound 36 (162 mg, 89%).

$[\alpha]^{20}_D$=+29 (c=1.05, dichloromethane)

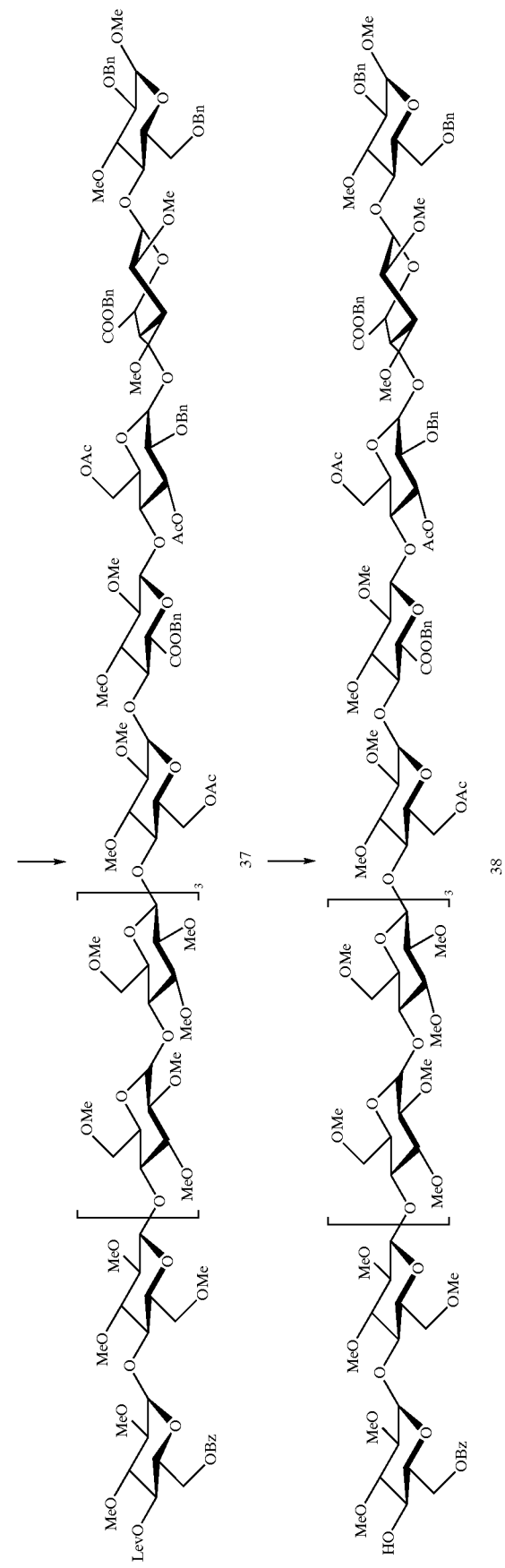

Preparation 33

Methyl O-(6-O-benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)-]₃-O-(6-O-acetyl-2,3-di-O-methyl-α-D-glucopyranosyl)-(1→4)-O-(benzyl 2,3-di-O-methyl-β-D-glucopyranosyluronate)-(1→4)-O-(3,6-di-O-acetyl-2-O-benzyl-α-D-glucopyranosyl)-(1→4)-O-(benzyl 2,3-di-O-methyl-α-L-idopyranosyluronate -(1→4)-2,6-di-O-benzyl-3-O-methyl-α-D-glucopyranoside (37)

The imidate 27 (177 mg, 76.6 μmol) and the acceptor 36 (201 mg, 0.15 mmol) in a 2/1 diethyl ether/dichloromethane mixture (2.8 ml) are treated with tert-butyldimethylsilyl trifluoromethanesulphonate (11.5 μl of a 1 molar solution in dichloromethane) as for the synthesis of compound 35. The compound is purified on a Sephadex® LH-20 chromatography column (1/1 dichloromethane/ethanol) and then on a column of silica (3/0.5/1 toluene/acetone/ethanol) and finally on a column of silica (3/2 diisopropyl ether/ethanol) to give the derivative 37 (116 mg, 44%).

TLC: Rf=0.31, silica gel, 3/0.5/0.4 v/v/v diisopropyl ether/acetone/ethanol.

Preparation 34

Methyl O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)-]₃-O-(6-O-acetyl-2,3-di-O-methyl-α-D-glucopyranosyl)-(1→4)-O-(benzyl 2,3-di-O-methyl-β-D-glucopyranosyl-uronate)-(1→4)-O-(3,6-di-O-acetyl-2-O-benzyl-α-D-glucopyranosyl)-(1→4)-O-(benzyl 2,3-di-O-methyl-α-L-idopyranosyluronate-(1→4)-2,6-di-O-benzyl-3-O-methyl-α-D-glucopyranoside (38)

Compound 37 (110 mg, 0.032 mmol) is converted into compound 38 (95 mg, 89%) according to the procedure described for the preparation of compound 36.

TLC: Rf=0.32, silica gel, 1/1 v/v toluene/acetone

SCHEME 9

Synthesis of the trisaccharide 43

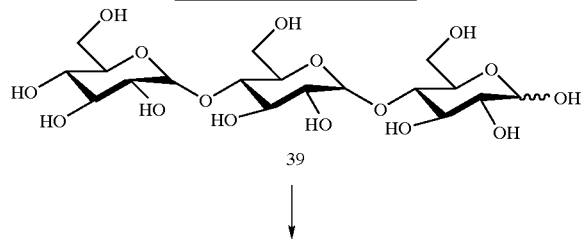

39

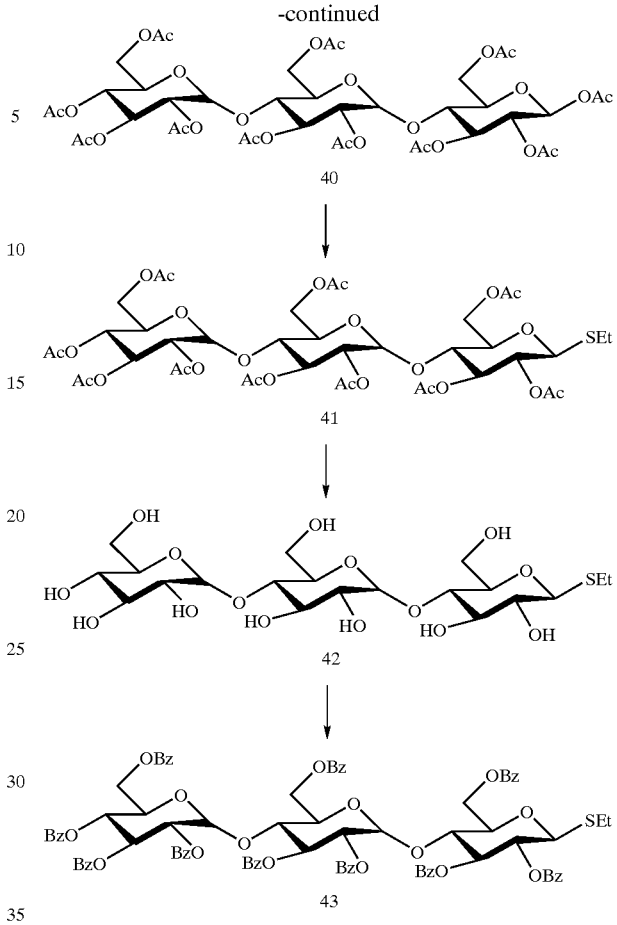

Preparation 35

O-(2,3,4,6-Tetra-O-acetyl-α-D-glucopyranosyl)-(1→4)-O-(2,3,6-tri-O-acetyl-α-D-glucopyranosyl)-(1→4)-1,2,3,6-tetra-O-acetyl-β-D-glucopyranose (40)

Commercial maltotriose (7 g, 13.9 mmol) is added portionwise to a suspension of sodium acetate (7 g, 85 mmol) in acetic anhydride (70 ml) at 155° C. After 15 minutes, the solution is cooled and poured into ice-cold water (700 ml). After extraction with ethyl acetate, the organic phase is washed with water, dried over magnesium sulphate, filtered and concentrated to give 13.1 g of compound 40.

TLC: Rf=0.53, silica gel, 7/3 v/v dichloromethane/ethyl acetate

Preparation 36

Ethyl O-(2,3,4,6-tetra-O-acetyl-α-D-glucopyranosyl)-(1→4)-O-(2,3,6-tri-O-acetyl-α-D-glucopyranosyl)-(1→4)-2,3,6-tri-O-acetyl-1-thio-β-D-glucopyranoside (41)

Compound 40 (13 g, 13.5 mmol) is dissolved in toluene (80 ml). Ethanethiol (1.97 ml, 26.9 mmol) and boron trifluoride diethyl etherate (13.7 ml of a molar solution in toluene) are added under a nitrogen atmosphere. After stirring for 60 hours, the mixture is diluted with water and dichloromethane. After extraction, the organic phase is washed with 10% sodium hydrogen carbonate solution and water, dried, filtered and concentrated. The crude product is purified by chromatography on a column of silica gel to give 8.6 g of compound 41.

TLC: Rf=0.60, silica gel, 7/3 v/v dichloromethane/ethyl acetate

Preparation 37

Ethyl O-(α-D-glucopyranosyl)-(1→4)-O-(α-D-glucopyranosyl)-(1→4)-1-thio-β-D-glucopyranoside (42)

Compound 41 is converted into compound 42 according to the procedure described for the preparation of compound 5.

TLC: Rf=0.80, silica gel, 13/7/1.6/4 v/v/v/v ethyl acetate/pyridine/acetic acid/water Preparation 38

Ethyl O-(2,3,4,6-tetra-O-benzoyl-α-D-glucopyranosyl)-(1→4)-O-(2,3,6-tri-O-benzoyl-α-D-glucopyranosyl)-(1→4)-2,3,6-tri-O-benzoyl-1-thio-β-D-glucopyranoside (43)

Compound 42 is converted into compound 43 according to the procedure described for the preparation of compound 2.

SCHEME 10
Preparation of the polysaccharide 46
43 + 38 →
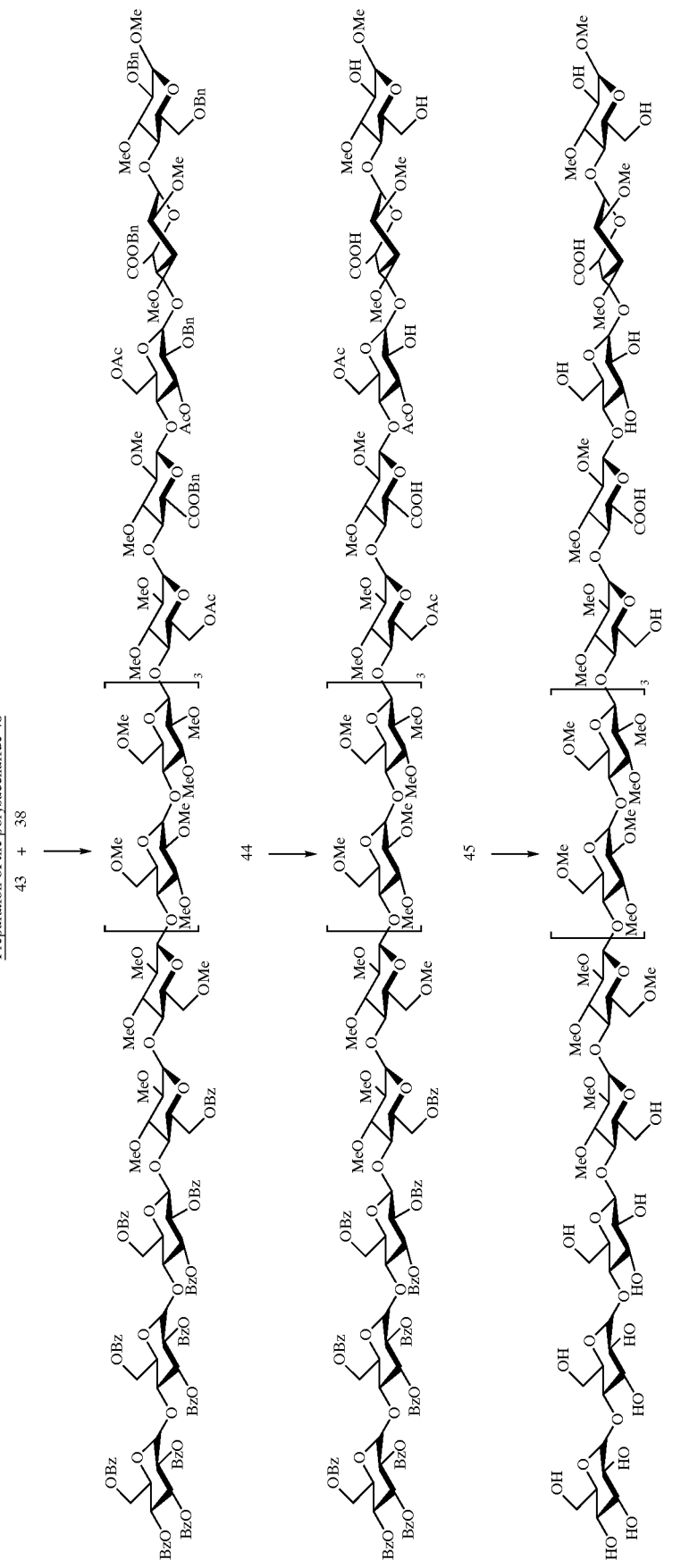

Preparation 39

Methyl O-(2,3,4,6-tetra-O-benzoyl-α-D-glucopyranosyl)-(1→4)-O-(2,3,6-tri-O-benzoyl-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-O-(6-O-acetyl-2,3-di-O-methyl-α-D-glucopyranosyl)-(1→4)-O-(benzyl 2,3-di-O-methyl-β-D-glucopyranosyluronate)-(1→4)-O-(3,6-di-O-acetyl-2-O-benzyl-α-D-glucopyranosyl-(1→4)-O-(benzyl 2,3-di-O-methyl-α-L-idopyranosyluronate)-(1→4)-2,6-di-O-benzyl-3-O-methyl-α-D-glucopyranoside (44)

The thioglycoside 43 (170 mg, 106.7 μmol) and the acceptor 38 (90 mg, 27 μmol) are coupled according to the procedure described for compound 4. The product is first purified by chromatography on Sephadex® LH 20 (1/1 dichloromethane/ethanol), followed by chromatography on a column of silica gel (12/10 v/v cyclohexane/acetone) to give 89.5 mg (68%) of compound 44.

TLC: Rf=0.43, silica gel, (12/10 v/v cyclohexane/acetone)

Preparation 40

Methyl O-(2,3,4,6-tetra-O-benzoyl-α-D-glucopyranosyl)-(1→4)-O-(2,3,6-tri-O-benzoyl-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-O-(6-O-acecyl-2,3-di-O-methyl-α-D-glucopyranosyl-(1→4)-O-(2,3-di-O-methyl-β-D-gluco-pyranosyluronic acid)-(1→4)-O-(3,6-di-O-acetyl-α-D-glucopyranosyl-(1→4)-O-(2,3-di-O-methyl-α-L-ido-pyranosyluronic acid)-(1→4)-3-O-methyl-α-D-gluco-pyranoside(45)

A solution of compound 44 (80 mg, 0.0163 mmol) in acetic acid (3 ml) is treated under hydrogen pressure (10 bar) in the presence of 10% palladium on charcoal (160 mg). After filtration, the solution is concentrated and gives compound 45, which is used in the following step without purification.

Preparation 41

Methyl O-(α-D-glucopyranosyl)-(1→4)-O-(α-D-glucopyranosyl)-(1→4)-O-(β-D-glucopyranosyl)-(1→4)-O-(2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-gluopyranosyl)-(1→4)]₃-O-(2,3-di-O-methyl-α-D-glucopyranosyl)-(1→4)-O-(2,3-di-O-methyl-β-D-glucopyranosyluronic acid)-(1→4)-O-(α-D-glucopyranosyl)-(1→4)-O-(2,3-di-O-methyl-α-L-idopyranosyluronic acid)-(1→4)-3-O-methyl-α-D-glucopyranoside (46)

A mixture of methanol (2.8 ml) and of 5N sodium hydroxide solution (0.69 ml) is added to compound 45 (72 mg, 0.016 mmol). Aqueous 5M sodium hydroxide solution is added (in an amount such that the concentration of sodium hydroxide is 0.5M at the end of the addition) to a solution of an ester in methanol (150 ml/mmol). After 2–5 hours, water is introduced and the mixture is passed through a column of Sephadex® G-25 gel (1.6×115 cm) eluted with water. The eluate is concentrated and passed through a Dowex® 50H⁺ column (2 ml) and freeze-dried. At this stage, confirmation that all of the protecting groups have been removed is made by proton NMR. If necessary, the product is resubjected to the hydrogenation and/or saponification. Compound 46 (34 mg, 68% in two steps) is thus obtained.

SCHEME 11

Preparation of the disaccharide 54

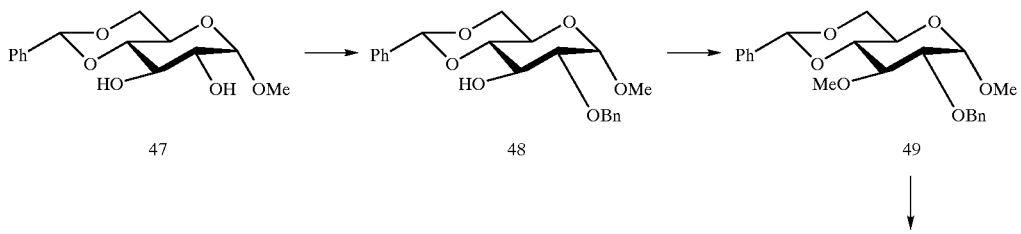

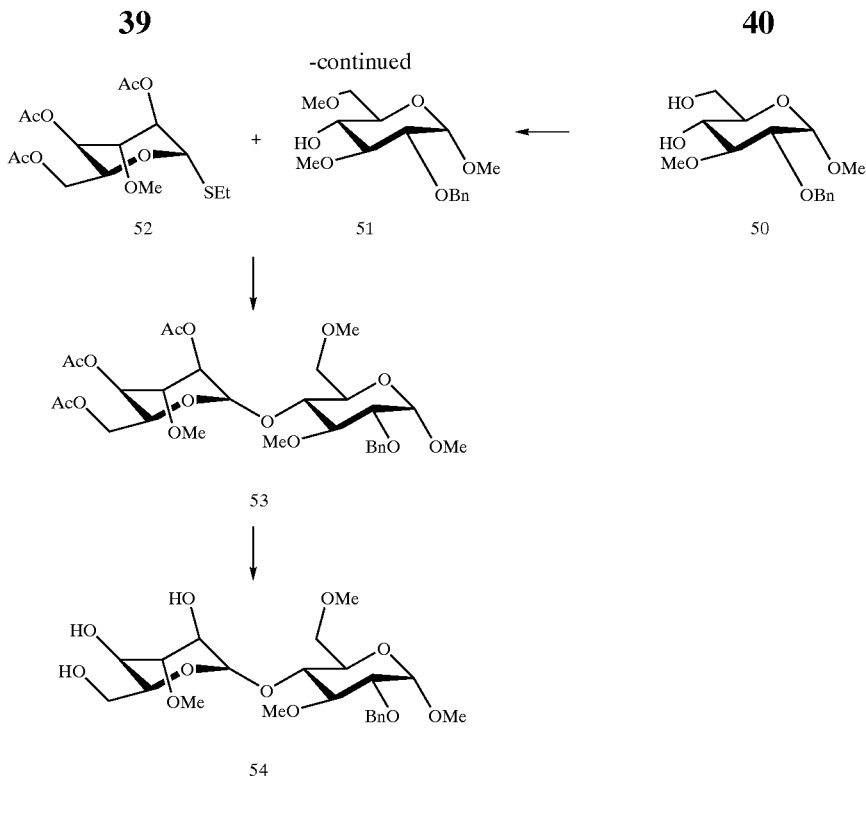

Preparation 42

Methyl O-4,6-O-benzylidene-2-O-benzyl-α-D-glucopyranoside (48)

Compound 47 (60 g) (commercially available) is dissolved in N,N-dimethylformamide (858 ml) with benzyl bromide (50.5 ml). The solution is cooled to +10° C. and aqueous 20% sodium hydroxide solution is added dropwise while stirring the mixture. After 1 hour, the reaction temperature is raised to 20° C. and the mixture is left stirring for a further 20 hours. The solution is then poured into a mixture of water and ice and toluene, and extracted. The organic phase is concentrated and the crude product is purified by crystallization to give 30.0 g of compound 48, described by J. M. Küster et al. in Justus Liebigs Ann. Chem. 1975, 2179–2189.

TLC: Rf=0.60, silica gel, 7/3 v/v toluene/ethyl acetate

Preparation 43

Methyl O-4,6-O-benzylidene-2-O-benzyl-3-O-methyl-α-D-glucopyranoside (49)

Compound 48 (26.4 g) is dissolved in N,N-dimethylformamide (211 ml) and cooled to +5° C. Sodium hydride (3.2 g) is added under a nitrogen atmosphere. Next, iodomethane (11.3 g) is added dropwise and the mixture is stirred for 1 hour at room temperature. The mixture is diluted in ethyl acetate, washed twice with water and concentrated to give 28 g of the crude compound 49, described by M. Petitou et al. in J. Med. Chem. 1997, 40, 1600–1607.

TLC: Rf=0.70, silica gel (7/3 v/v toluene/ethyl acetate)

Preparation 44

Methyl O-2-O-benzyl-3-O-methyl-α-D-glucopyranoside (50)

Compound 49 (28 g) is dissolved in methanol (468 ml). p-Toluenesulphonic acid (1.35 g) is added and the mixture is stirred for 20 hours at 20° C. The mixture is diluted with toluene and concentrated. Purification by chromatography on a column of silica gel gives 21 g of compound 50.

TLC: Rf=0.07, silica gel (6/4 v/v toluene/ethyl acetate)

Preparation 45

Methyl O-2-O-benzyl-3,6-di-O-methyl-α-D-glucopyranoside (51)

Compound 50 (11.8 g) is dissolved in dichloromethane (160 ml) under a nitrogen atmosphere. Trimethyloxonium tetrafluoroborate (7.0 g) and 2,6-di-tert-butyl-4-methylpyridine (10.6 g) are added at room temperature. After 2 hours, the mixture is poured into a mixture of water and ice, and is extracted with dichloromethane. The organic phase is washed with sodium hydrogen carbonate and concentrated. Purification of the crude product by chromatography on silica gel gives 10.1 g of compound 51.

TLC: Rf=0.25, silica gel (7/3 v/v toluene/ethyl acetate).

Preparation 46

Ethyl 2,4,6-tri-O-acetyl-3-O-methyl-1-thio-α-L-idopyranose (52)

1,2,4,6-Tetra-O-acetyl-3-O-methyl-α-L-idopyranose (prepared as described for its per-benzoyl analogue by replacing benzoyl chloride with acetic anhydride; Jaurand et al. Bio. Med. Chem. Lett, 1992, 2, 897–900) (48.4 g) is dissolved in toluene (175 ml). Ethanethiol (20 ml) and boron trifluoride etherate (1M in toluene, 134 ml) are added under a nitrogen atmosphere. After stirring for 1 hour, aqueous sodium hydrogen carbonate (400 ml) and the mixture is added and the mixture is stirred for 1 hour. The mixture is then poured into ethyl acetate. The organic phase is washed twice with water and concentrated. Purification by chromatography on a column of silica gel gives 29.6 g of compound 52.

TLC: Rf=0.45, silica gel (6/4 v/v toluene/ethyl acetate).

Preparation 47

Methyl O-(2,4,6-tri-O-acetyl-3-O-methyl-α-L-idopyranosyl)-(1→4)-2-O-benzyl-3,6-di-O-methyl-6-O-methyl-α-D-glucopyranoside (53)

Compound 51 (10.1 g) and compound 52 (16.0 g) are dissolved in toluene (304 ml) under a nitrogen atmosphere. After addition of powdered molecular sieves (4 Å), the reaction medium is cooled to −20° C. A freshly prepared 0.1M solution of N-iodosuccinimide (10.1 g) and of trifluoromethanesulphonic acid (0.80 ml) in a 1/1 v/v dioxane/dichloromethane mixture is added dropwise under a stream of nitrogen. After 10 minutes, the red reaction mixture is filtered and washed successively with aqueous sodium thiosulphate and aqueous sodium hydrogen carbonate. The organic phase is concentrated and the residue is purified by chromatography on silica gel to give 21.1 g of compound 53.

TLC: Rf=0.30, silica gel (6/4 v/v toluene/ethyl acetate).

Preparation 48

Methyl O-(3-O-methyl-α-L-idopyranosyl)-(1→4)-2-O-benzyl-3,6-di-O-methyl-α-D-glucopyranoside (54)

Compound 53 (21.1 g) is dissolved in 295 ml of a methanol/dioxane mixture (1/1 v/v) and potassium tert-butoxide is added. After 30 minutes, the mixture is neutralized with Dowex® 50WX8 resin in H⁺ form and concentrated under vacuum. Purification is carried out by chromatography on silica gel, to give 12.7 g of compound 54.

TLC: Rf=0.08, silica gel (3/7 v/v toluene/ethyl acetate)

SCHEME 12

Preparation of the tetrasaccharide 62

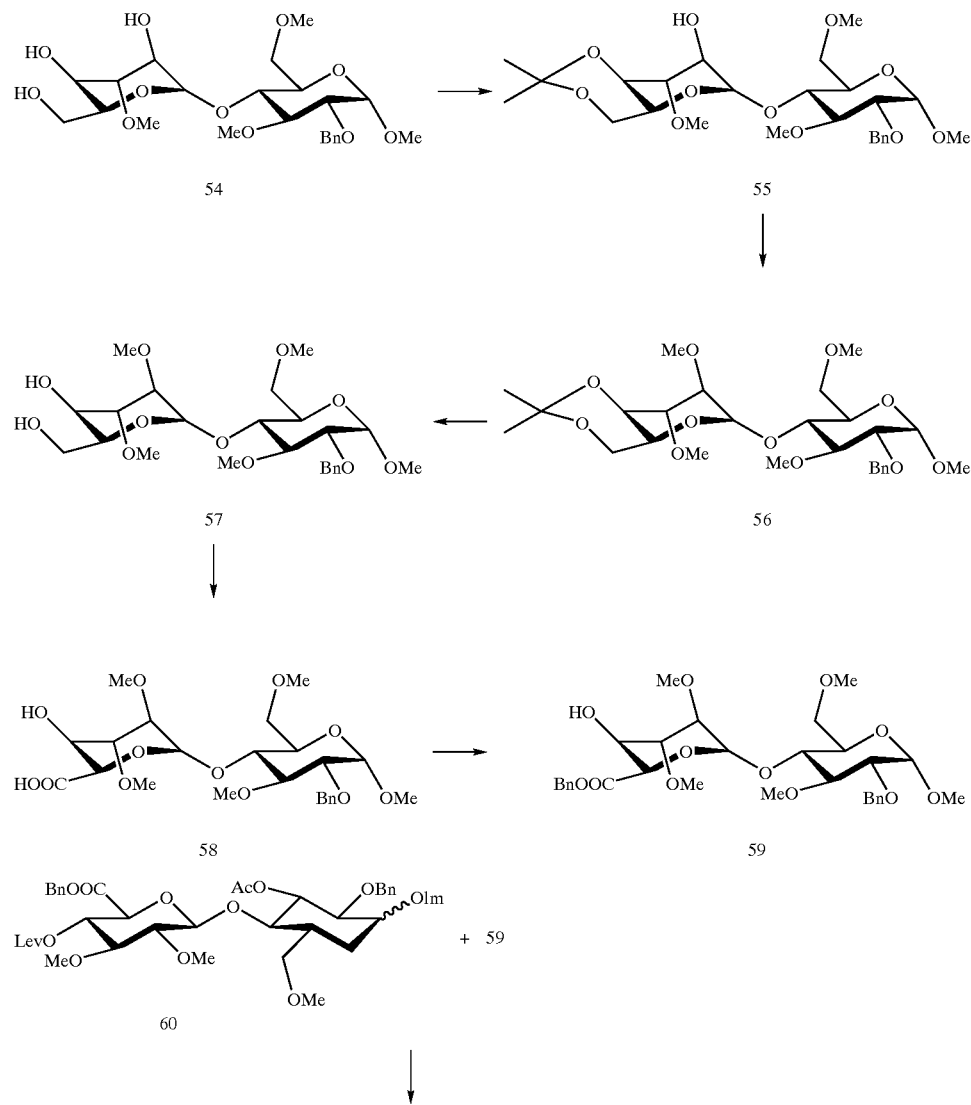

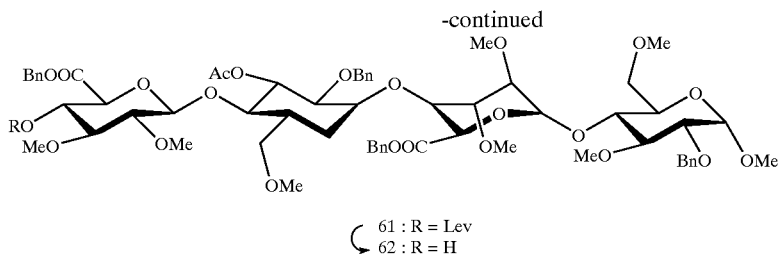

$\begin{matrix} 61 : R = Lev \\ 62 : R = H \end{matrix}$

Preparation 49

Methyl O-(4,6-O-isopropylidene-3-O-methyl-α-L-idopyranosyl)-(1→4)-2-O-benzyl-3,6-di-O-methyl-α-D-glucopyranoside (55)

Compound 54 (12.7 g) is dissolved in tetrahydrofuran (67 ml) under a nitrogen atmosphere. 2,2-Dimethoxypropane (19 ml) and p-toluenesulphonic acid are added and the mixture is then stirred for 16 hours at room temperature. The reaction medium is then diluted with aqueous sodium hydrogen carbonate and extracted with ethyl acetate to give, after evaporation of the solvent, a crude residue which is purified by chromatography on silica gel to give 10.4 g of compound 55.

TLC: Rf=0.35, silica gel (1/1 v/v toluene/ethyl acetate).

Preparation 50

Methyl O-(4,6-O-isopropylidene-2,3-di-O-methyl-α-L-idopyranosyl)-(1→4)-2-O-benzyl-3,6-di-O-methyl-α-D-glucopyranoside (56)

Compound 55 (10.4 g) is dissolved in tetrahydrofuran (140 ml) and cooled to 10° C. Sodium hydride (1.38 g; 60% dispersion in oil) and iodomethane (1.84 ml) are added under a nitrogen atmosphere. After 4 hours, the excess sodium hydride is destroyed with methanol and the mixture is extracted with dichloromethane and concentrated. The residue is purified by chromatography on silica gel, to give 11.1 g of compound 56.

TLC: Rf=0.55, silica gel (95/5 v/v toluene/ethyl acetate).

Preparation 51

Methyl O-(2,3-di-O-methyl-α-L-idopyranosyl)-(1→4)-2-O-benzyl-3,6-di-O-methyl-α-D-glucopyranoside (57)

Compound 56 (11.1 g) is dissolved in a 7/3 (v/v) acetic acid/water mixture and stirred overnight. The mixture is evaporated twice in the presence of toluene and purified by chromatography on silica gel, to give 9.2 g of compound 57.

TLC: Rf=0.09, silica gel (1/1 v/v toluene ethyl acetate).

Preparation 52

Methyl O-(2,3-di-O-methyl-α-L-idopyranosyluronic acid)-(1→4)-2-O-benzyl-3,6-di-O-methyl-α-D-glucopyranoside (58)

2,2,6,6-Tetramethyl-1-piperidinyloxy (13 mg), saturated sodium hydrogen carbonate solution (16 ml), potassium bromide (88 mg) and tetrabutylammonium chloride (117 mg) are added to a solution of compound 57 (4.7 g) in dichloromethane (28 ml). The mixture is cooled to 0° C. and a mixture of saturated sodium chloride solution (17.8 ml), of saturated sodium hydrogen carbonate solution (8.8 ml) and of sodium hypochlorite (1.3M; 20 ml) is added over 15 minutes. After stirring for 1 hour, the medium is diluted with ethyl acetate, washed with saturated aqueous sodium chloride solution, dried over magnesium sulphate, filtered and evaporated to dryness to give 3.5 g of the crude compound 58.

TLC: Rf=0.14, silica gel, 9/1 v/v dichloromethane/methanol.

Preparation 53

Methyl O-(benzyl-2,3-di-O-methyl-α-L-idopyranosyluronate)-(1→4)-2-O-benzyl-3,6-di-O-methyl-α-D-glucopyranoside (59)

Compound 58 (3.5 g) is dissolved in N,N-dimethylformamide (29 ml) under a nitrogen atmosphere. Potassium hydrogen carbonate (1.76 g) and benzyl bromide (2.85 ml) are added and the mixture is stirred for 4 hours. Ethyl acetate and water are added and, after extraction, the organic phase is concentrated. Purification by chromatography on silica gel gives 3.4 g of compound 59.

TLC: Rf=0.43, silica gel, 4/6 v/v toluene/ethyl acetate

Preparation 54

Methyl O-(benzyl 4-O-levulinoyl-2,3-di-O-methyl-β-D-glucopyranosyluronate)-(1→4)-O-(3-O-acetyl-2-O-benzyl-6-O-methyl-α-D-glucopyranosyl)-(1→4)-O-(benzyl 2,3-di-O-methyl-α-L-idopyranosyluronate)-(1→4)-2-O-benzyl-3,6-di-O-methyl-α-D-glucopyranoside (61)

A mixture of compound 59 (0.53 g) and compound 60 (1.0 g) is evaporated in the presence of toluene and dissolved in dichloromethane (16.2 ml) under a nitrogen atmosphere. After addition of powdered molecular sieves (4 Å), the mixture is cooled to −20° C. After stirring for 15 minutes, trimethylsilyl trifluoromethanesulph-onate (15 mol% relative to compound 60) is added. After 15 minutes, the mixture is treated with aqueous sodium hydrogen carbonate. After filtering off the molecular sieves, the filtrate is diluted with dichloromethane, washed with water, concentrated and purified by chromatography on silica gel to give 0.75 g of compound 61.

NMR: Rf=0.45, silica gel (3/7 v/v toluene/ethyl acetate).

Preparation 55

Methyl O-(benzyl 2,3-di-O-methyl-β-D-glucopyrano-syluronate)-(1→4)-O-(3-O-acetyl-2-O-benzyl-6-O-methyl-α-D-glucopyranosyl)-(1→4)-O-(benzyl-2,3-di-O-methyl-α-L-idopyranosyluronate)-(1→4)-2-O-benzyl-3,6-di-O-methyl-α-D-glucopyranoside (62)

Compound 61 (0.74 g) is dissolved in pyridine (3.0 ml) and a mixture of acetic acid (4.1 ml) and hydrazine hydrate (0.47 ml) in pyridine (3.0 ml) is added at room temperature.

After stirring for 9 hours, dichloromethane and water are added. The organic phase is separated out and washed successively with hydrochloric acid solution (1.0N), aqueous sodium hydrogen carbonate and water. The organic phase is concentrated and purified by chromatography on silica gel to give 0.66 g of compound 62.

TLC: Rf=0.25, silica gel (98/2 v/v dichloromethane/methanol).

The tetrasaccharide 68 below is prepared in a similar manner according to Reaction Scheme 13 below, starting with the disaccharide 55.

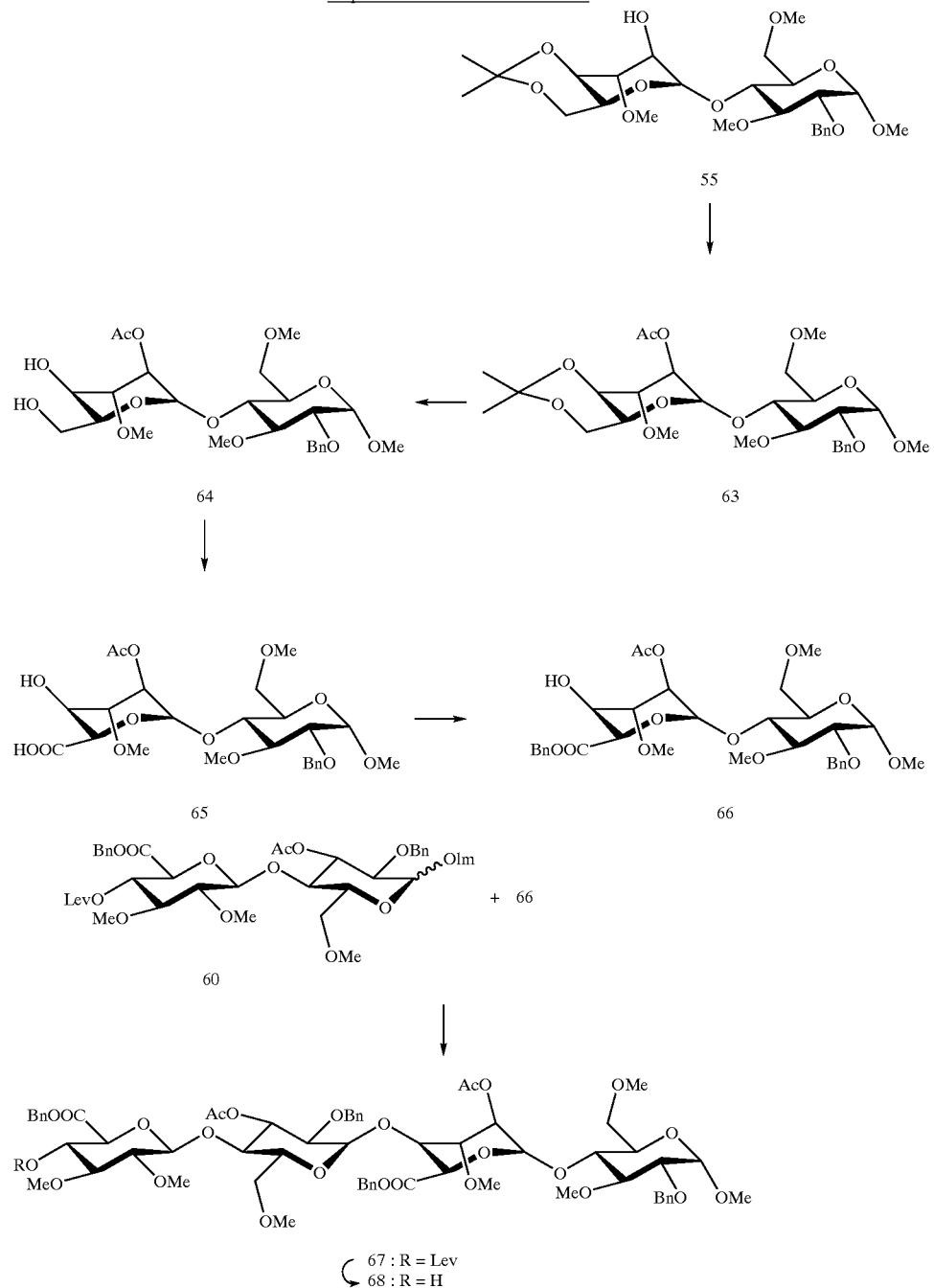

SCHEME 14

Preparation of the disaccharide 75

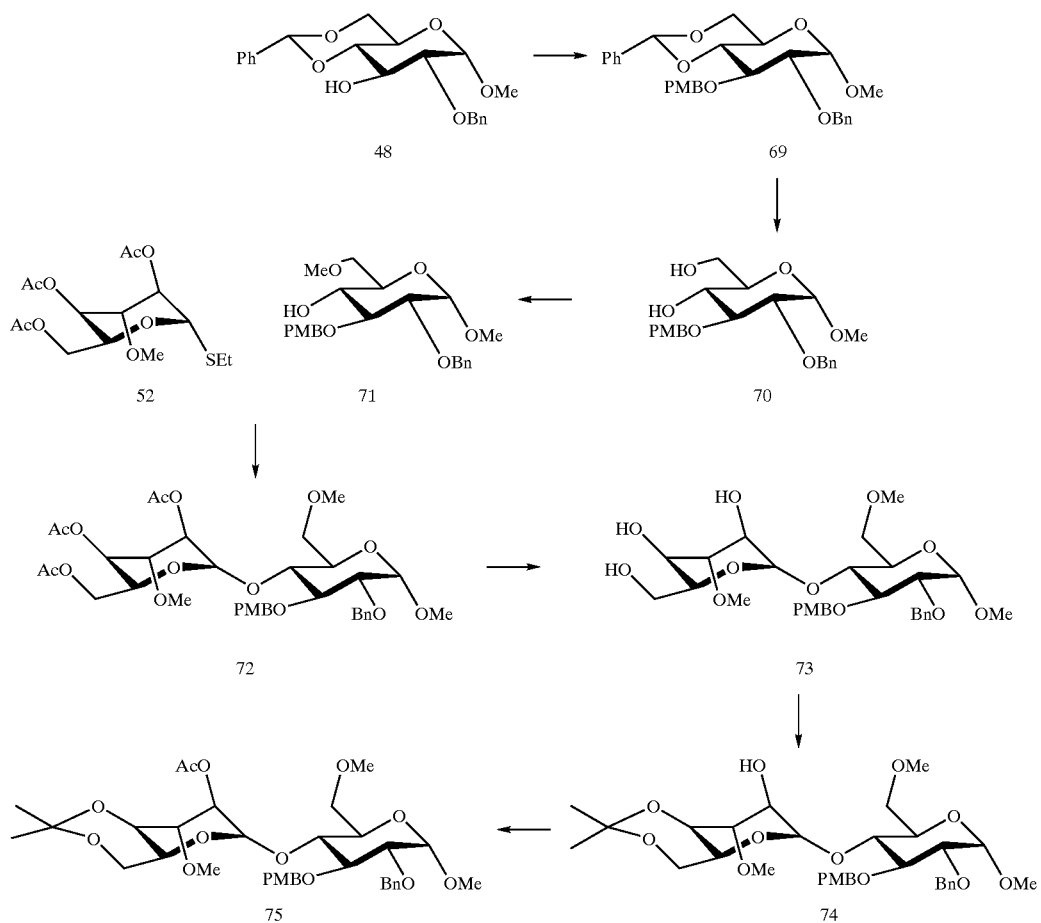

Preparation 56

Methyl 2-O-benzyl-4,6-di-O-benzylidene-3-O-p-methoxy-benzyl-α-D-glucopyranoside (69)

Compound 48 (26.4 g) is dissolved in N,N-dimethylformamide (211 ml) and cooled to 5° C. Sodium hydride (2.5 g) is added under a nitrogen atmosphere. Next, 4-methoxybenzyl chloride (13.3 g) is added dropwise and the mixture is stirred for 1 hour at room temperature. The mixture is diluted with ethyl acetate, washed twice with water and concentrated to give 40.7 g of compound 69.

TLC: Rf=0.80, silica gel, 7/3 v/v toluene/ethyl acetate

Preparation 57

Methyl 2-O-benzyl 3-O-p-methoxybenzyl-α-D-glucopyranoside (70)

Compound 69 (34.9 g) is dissolved in aqueous 60% acetic acid and stirred for 4 hours at 60° C. The mixture is diluted with toluene and concentrated. Purification by chromatography on a column of silica gel gives 26.4 g of compound 70.

TLC: Rf=0.07, silica gel, 7/3 v/v toluene/ethyl acetate

Preparation 58

Methyl 2-O-benzyl-3-O-p-methoxybenzyl-6-O-methyl-α-D-glucopyranoside (71)

Compound 70 (26.4 g) is dissolved in dichloromethane (263 ml) under a nitrogen atmosphere. Trimethyloxonium tetrafluoroborate (11.6 g) and 2,6-di-tert-butyl-4-methylpyridine (17.4 g) are added at room temperature. After 4 hours, the mixture is poured onto ice-cold water and extracted with dichloromethane. The organic phase is washed with sodium hydrogen carbonate and concentrated. Purification of the crude product by chromatography on a column of silica gel gives 18.5 g of compound 71.

TLC: Rf=0.25, silica gel, 7/3 v/v toluene/ethyl acetate

Preparation 59

Methyl O-(2,4,6-tri-O-acetyl-3-O-methyl-α-L-idopyranosyl)-(1→4)-2-O-benzyl-3-O-p-methoxybenzyl-6-O-methyl-α-D-glucopyranoside (72)

Compound 71 (17.5 g) and compound 52 (28.2 g) are dissolved in toluene (525 ml) under a nitrogen atmosphere. After addition of a 4 Å molecular sieve, the reaction is cooled to −20° C. A freshly prepared 0.1M solution of N-iodosuccinimide (17.4 g) and of trifluoromethanesulphonic acid (1.38 ml) in 1/1 v/v dioxane/dichloromethane is added dropwise under a continuous stream of nitrogen. After 10 minutes, the red reaction mixture is filtered and washed successively with aqueous sodium thiosulphate and aqueous sodium hydrogen carbonate. The organic phase is concentrated under vacuum and 30.0 g of compound 72 are isolated.

Preparation 60

Methyl O-(3-O-methyl-α-L-idopyranosyl)-(1→4)-2-O-benzyl-3-O-p-methoxybenzyl-6-O-methyl-α-D-glucopyranoside (73)

Compound 72 (30.0 g) is dissolved in 460 ml of 1/1 v/v methanol/dioxane and potassium tert-butoxide is added. After 15 minutes, the mixture is neutralized with Dowex® 50WX8H⁺ resin and concentrated under vacuum. Purification is performed by chromatography on a column of silica gel, to give 17.4 g of compound 73.

TLC: Rf=0.25, silica gel 95/5 v/v dichloromethane/methanol

Preparation 61

Methyl O-(4,6-O-isopropylidene-3-O-methyl-α-L-ido-pyranosyl)-(1→4)-2-O-benzyl-3-O-p-methoxybenzyl-6-O-methyl-α-D-glucopyranoside (74)

Compound 73 (17.4 g) is dissolved in N,N-dimethylformamide (77 ml) under a nitrogen atmosphere. 2,2-Dimethoxypropane (26 ml) and p-toluenesulphonic acid are added and the mixture is then stirred for 30 minutes. Dilution of the mixture with aqueous sodium hydrogen carbonate and then extraction with ethyl acetate gives, after evaporation of the solvent, 19.7 g of compound 74.

TLC: Rf=0.45, silica gel, 95/5 v/v dichloromethane/methanol

Preparation 62

Methyl O-(4,6-O-isopropylidene-2,3-di-O-methyl-α-L-idopyranosyl)-(1→4)-2-O-benzyl-6-O-methyl-α-D-glucopyranoside (75)

Compound 74 (18.5 g) is dissolved in N,N-dimethylformamide (24.4 ml) and cooled to 0° C. Sodium hydride (1.47 g; 60% dispersion in oil) and iodomethane (2.36 ml) are added, under a nitrogen atmosphere. After 1 hour, the excess sodium hydride is destroyed with methanol and the mixture is extracted with dichloromethane and concentrated to give 20.0 g of compound 75.

TLC: Rf=0.85, silica gel, 95/5 v/v dichloromethane/methanol.

SCHEME 15

Synthesis of the disaccharide 60

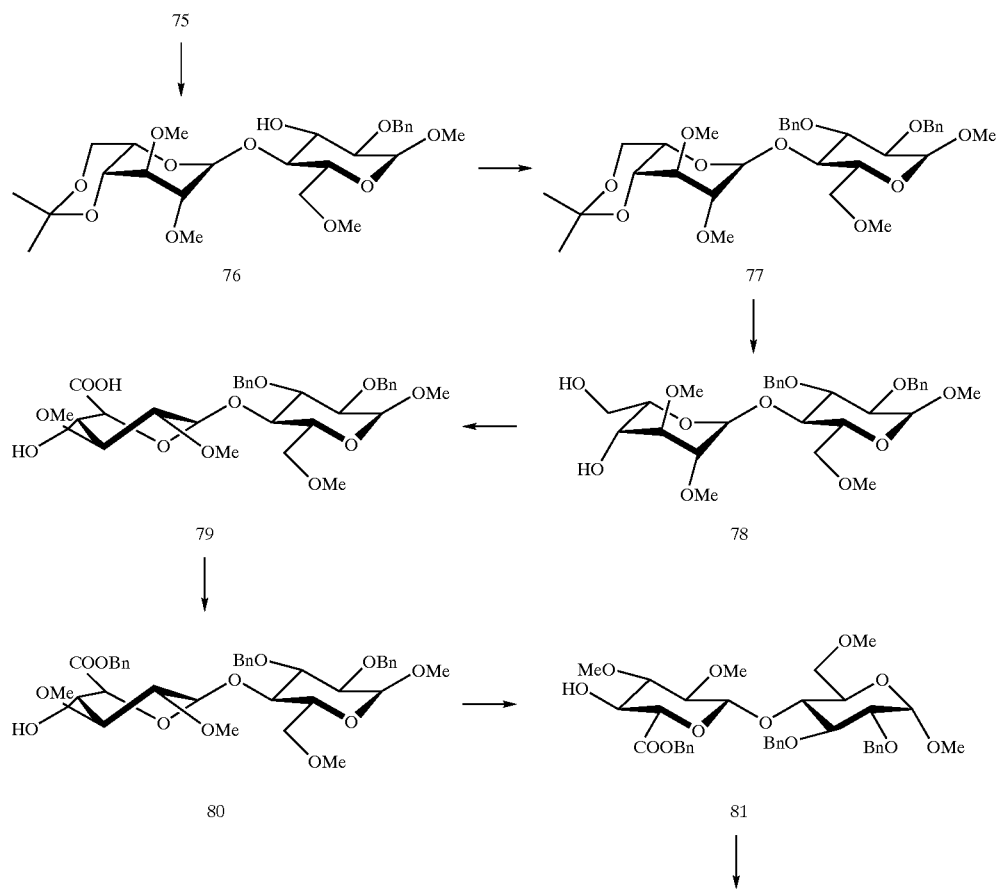

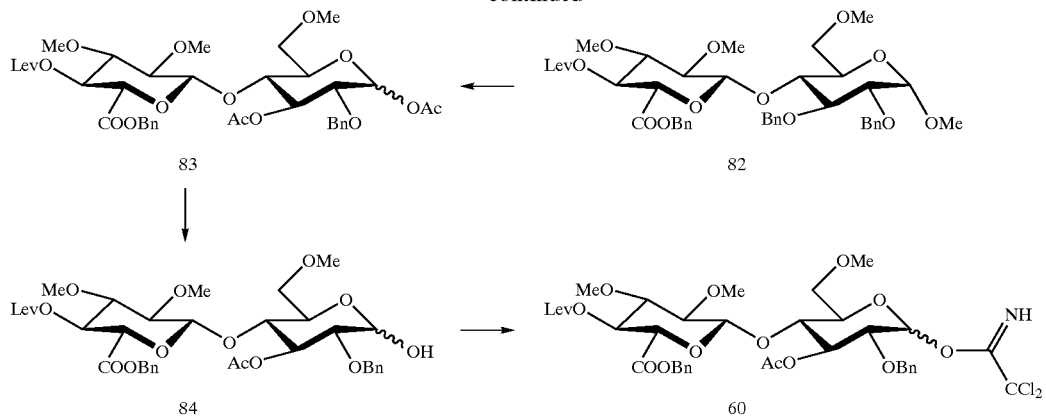

Preparation 63

Methyl O-(4,6-O-isopropylidene-2,3-di-O-methyl-
α-L-idopyranosyl)-(1→4)-2-O-benzyl-6-O-methyl-
α-D-glucopyranoside (76)

Compound 75 (18.4 g) is dissolved in dichloromethane (838 ml) and water (168 ml). 2,3-Dichloro-5,6-dicyano-1,4-benzoquinone (7.1 g) is added and the mixture is stirred for 18 hours at 4° C. The mixture is poured into aqueous sodium hydrogen carbonate and extracted with dichloromethane. Concentration of the organic phase gives 12.7 g of compound 76.

TLC: Rf=0.40, silica gel, 95/5 v/v dichloromethane/methanol.

Preparation 64

Methyl O-(4,6-O-isopropylidene-2,3-di-O-methyl-
α-L-idopyranosyl)-(1→4)-2,3-di-O-benzyl-6-O-
methyl-α-D-glucopyranoside (77)

Compound 76 (10.5 g) is dissolved in dry N,N-dimethylformamide (178 ml) and then cooled to 0° C. under a nitrogen atmosphere. Sodium hydride (1.91 g; 60% dispersion in oil) is added, followed by dropwise addition of benzyl bromide (3.3 ml). After 30 minutes, the reaction is complete and the excess sodium hydride is destroyed with methanol. Water is added and the mixture is extracted twice with ethyl acetate. Evaporation of the solvent gives 13.6 g of compound 77.

TLC: Rf=0.50, silica gel, 1/1 v/v toluene/ethyl acetate.

Preparation 65

Methyl O-(2,3-di-O-methyl-α-L-idopyranosyl)-
(1→4)-2,3-di-O-benzyl-6-O-methyl-α-D-
glucopyranoside (78)

Compound 77 is dissolved in 77/33 (v/v) acetic acid/water and stirred overnight. The mixture is co-evaporated twice with toluene and purified by chromatography on a column of silica gel, to give 11.5 g of compound 78.

TLC: Rf=0.09, silica gel, 1/1 v/v toluene/ethyl acetate.
Rf=0.68, silica gel, 9/1 v/v dichloromethane/methanol.

Preparation 66

Methyl O-(2,3-di-O-methyl-α-L-idopyranosyluronic
acid)-(1→4)-2,3-di-O-benzyl-6-O-methyl-α-D-
glucopyranoside (79)

2,2,6,6-Tetramethyl-1-piperidyloxy (33 mg), sodium hydrogen carbonate solution (40 ml), potassium bromide (218 mg) and tetrabutylammonium chloride (289 mg) are added to a solution of compound 78 (11.6 g) in dichloromethane (60 ml). The mixture is cooled to 0° C. and a mixture of saturated sodium chloride solution (44 ml), of saturated sodium hydrogen carbonate solution (21.8 ml) and of sodium hypochlorite (1.3M, 50 ml) is added over 15 minutes. After stirring for 1 hour, the mixture is diluted with water and extracted (3 times) with dichloromethane. The organic phase is washed with aqueous sodium chloride solution, dried over magnesium sulphate, filtered and evaporated to dryness to give 13.4 g of the crude compound 79.

TLC: Rf=0.14, silica gel, 9/1 v/v dichloromethane/methanol.

Preparation 67

Methyl O-(benzyl 2,3-di-O-methyl-α-D-
idopyranosyluronate)-(1→4)-2,3-di-O-benzyl-6-O-
methyl-α-D-glucopyranoside (80)

Compound 79 is dissolved in N,N-dimethylformamide (110 ml) under a nitrogen atmosphere. Potassium hydrogen carbonate (6.7 g) and benzyl bromide (10.7 ml) are added and the mixture is stirred for 90 minutes. Ethyl acetate and water are added and, after extraction, the organic phase is concentrated. Purification by chromatography on a column of silica gel gives 9.9 g of compound 80.

TLC: Rf=0.43, silica gel, 4/6 v/v toluene/ethyl acetate.

Preparation 68

Methyl O-(benzyl 2,3-di-O-methyl-β-D-
glucopyranosyluronate)-(1→4)-2,3-di-O-benzyl-6-
O-methyl-α-D-glucopyranoside (81)

Compound 80 (9.9 g) is dissolved in 300 ml of methanol and refluxed under a nitrogen atmosphere. 1M sodium methoxide in methanol (65.2 ml) is added dropwise and the mixture is stirred and refluxed for 3 hours. The mixture is then cooled to room temperature, 1N sodium hydroxide (22.2 ml) is added and the reaction mixture is stirred for a further 90 minutes. After neutralization with Dowex® 50WX8 H⁺ resin and filtration, the mixture is concentrated. The pure product is dissolved in N,N-dimethylformamide (192 ml) and a molecular sieve is added under a nitrogen atmosphere. Potassium hydrogen carbonate (3.2 g) and benzyl bromide (4.8 ml) are added and the mixture is stirred for 5 hours. After addition of ethyl acetate and water, and extraction and separation of the two phases, the organic phase is concentrated. The crude product is purified by chromatography on a column of silica gel to give 6.19 g of compound 81 and 1.88 g of the starting compound 80.

TLC: Rf=0.55, silica gel, 4/6 v/v toluene/ethyl acetate.

Preparation 69

Methyl O-(benzyl-4-O-levulinoyl-2,3-di-O-methyl-β-D-glucopyranosyluronate)-(1→4)-2,3-di-O-benzyl-6-O-methyl-α-D-glucopyranoside (82)

Compound 81 (6.2 g) is dissolved in 40 ml of dioxane. Levulinic acid (2.1 g), dicyclohexylcarbodiimide (3.75 g) and 4-dimethylaminopyridine (0.2 g) are added and the mixture is stirred for 2 hours under a nitrogen atmosphere. Diethyl ether (95 ml) is added and the precipitate is filtered off. The filtrate is washed with aqueous potassium hydrogen sulphate, dried over magnesium sulphate, filtered and concentrated. Crystallization from ether/heptane gives 6.2 g of compound 82.

TLC: Rf=0.26, silica gel, 95/5 v/v dichloromethane/acetone.

Preparation 70

O-(Benzyl-4-O-levulinoyl-2,3-di-O-methyl-β-D-glucopyranosyluronate)-(1→4)-1,3-di-O-acetyl-2-O-benzyl-6-O-methyl-α,β-D-glucopyranose (83)

Compound 82 (6.1 g) is dissolved in acetic anhydride (256 ml) under a nitrogen atmosphere and cooled to −20° C. A mixture of sulphuric acid (4.9 ml) in acetic anhydride (49 ml) is added dropwise over 30 minutes. After 60 minutes, sodium acetate is added until a mixture of neutral pH is obtained. Ethyl acetate and water are then added and the organic phase is concentrated. Purification by chromatography on a column of silica gel gives 4.2 g of compound 83.

TLC: Rf=0.24, silica gel, 8/2 v/v dichloromethane/ethyl acetate

Preparation 71

O-(Benzyl 4-O-levulinoyl-2,3-di-O-methyl-β-D-glucopyranosyluronate)-(1→4)-3-O-acetyl-2-O-benzyl-6-O-methyl-α,β-D-glucopyranose (84)

Compound 83 (4.2 g) is dissolved in tetrahydrofuran (42 ml) and piperidine (4.1 ml) is added. The mixture is stirred overnight at room temperature. Ethyl acetate is added and the mixture is washed with 0.5N hydrochloric acid. The organic phase is concentrated and the residue is purified by chromatography on a column of silica gel to give 3.2 g of compound 84.

TLC: Rf=0.33, silica gel, 1/1 v/v dichloromethane/ethyl acetate.

Preparation 72

O-(Benzyl 4-O-levulinoyl-2,3-di-O-methyl-α-D-glucopyranosyluronate)-(1→4)-3-O-acetyl-2-O-benzyl-6-O-methyl-α,β-D-glucopyranose trichloroacetimidate (60)

Compound 84 (1.59 g) is dissolved in dry dichloromethane under a nitrogen atmosphere. Trichloroacetonitrile (1.1 ml) and caesium carbonate (72 mg) are added and the mixture is stirred for 1 hour. The caesium carbonate is filtered off and the filtrate is concentrated. Purification by chromatography on a column of silica gel gives 1.57 g of compound 60.

TLC: Rf=0.60, silica gel, 3/7 v/v toluene/ethyl acetate.

SCHEME 16

Synthesis of the tetrasaccharide 86

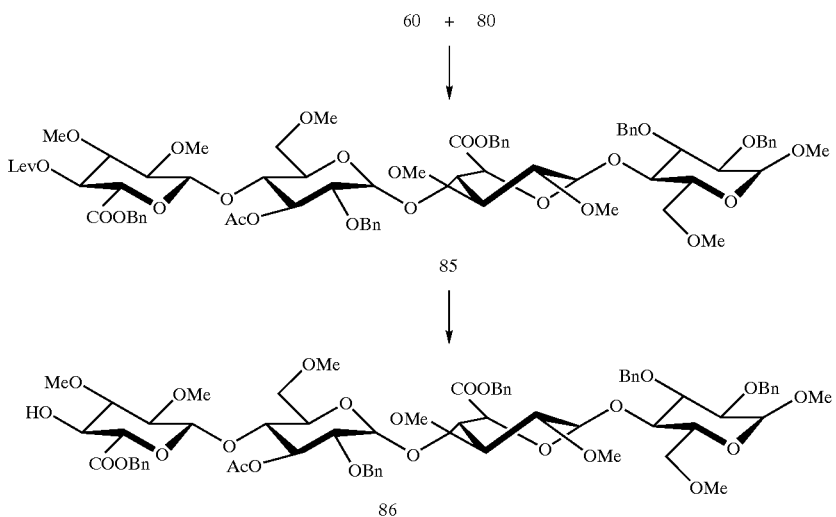

Preparation 73

Methyl O-(benzyl-4-O-levulinoyl-2,3-di-O-methyl-β-D-glucopyranosyluronate)-(1→4)-O-(3-O-acetyl-2-O-benzyl-6-O-methyl-α-D-glucopyranosyl)-(1→4)-O-(benzyl-2,3-di-O-methyl-α-L-idopyranosyluronate)-(1→4)-2,3-di-O-benzyl-6-O-methyl-α-D-glucopyranoside (85)

A mixture of compound 80 (300 mg) and compound 60 (455.6 mg) is co-evaporated with toluene and dissolved in dichloromethane (6 ml) under a nitrogen atmosphere. After addition of a 4 Å molecular sieve, the mixture is cooled to −20° C. After stirring for 20 minutes, trimethylsilyl trifluoromethanesulphonate (15 mol % relative to compound 60) is added. After 10 minutes, the mixture is neutralized with aqueous sodium hydrogen carbonate. After filtering off the molecular sieve, the filtrate is diluted with dichloromethane, washed with water, concentrated and purified by chromatography on a column of silica gel, to give 560 mg of compound 85.

TLC: Rf=0.50, silica gel, 3/7 v/v toluene/ethyl acetate.

Preparation 74

Methyl O-(benzyl 2,3-di-O-methyl-β-D-glucopyrano-syluronate)-(1→4)-O-(3-O-acetyl-2-O-benzyl-6-O-methyl-α-D-glucopyranosyl)-(1→4)-O-(benzyl 2,3-di-O-methyl-α-L-idopyranosyluronate)-(1→4)-2,3-di-O-benzyl-6-O-methyl-α-D-glucopyranoside (86)

Compound 85 (532.6 mg) is dissolved in pyridine (1.9 ml) and a mixture of acetic acid (2.4 ml) and hydrazine hydrate (0.3 ml) in pyridine (1.9 ml) is added at room temperature. After stirring for 9 minutes, dichloromethane and water are added. The organic phase is separated out and washed successively with 0.1N hydrochloric acid, aqueous sodium hydrogen carbonate and water. The organic phase is concentrated and purified by chromatography on a column of silica gel to give 451 mg of compound 86.

TLC: Rf=0.45, silica gel, 3/7 v/v toluene/ethyl acetate.

SCHEME 17

Synthesis of the monosaccharide 93

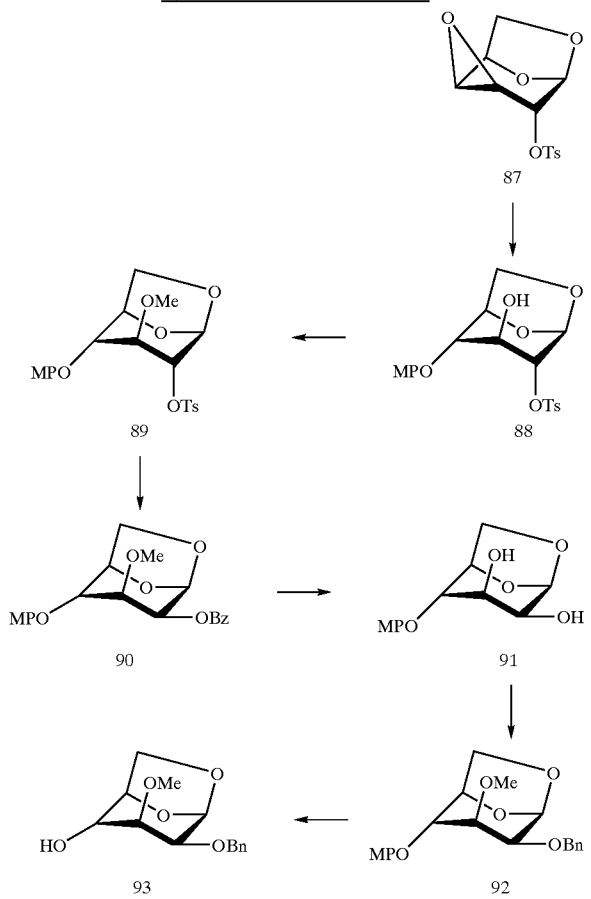

Preparation 75

1,6-Anhydro-4-O-p-methoxyphenyl-2-O-tosyl-β-D-glucopyranose (88)

A mixture of epoxide 87 (20 g, 67 mmol) (M. Cerny et al., Collect. Czech. Chem. Commun., 1961, 26, 2542) and of p-methoxyphenol (33.3 g, 268 mmol) is heated to 90° C. under argon. When the mixture becomes liquid, AlCl$_3$ (0.3 g, 2.35 mmol) is added portionwise and, after stirring for 30 minutes and recooling to room temperature, the reaction medium is diluted with dichloromethane (600 ml), neutralized with triethylamine (0.5 ml), washed with aqueous 1M sodium hydroxide solution (120 ml), saturated aqueous sodium chloride solution (3×60 ml), aqueous 10% potassium hydrogen sulphate solution (50 ml) and saturated aqueous sodium chloride solution. The organic phase is then dried (sodium sulphate), filtered and concentrated. The residue is purified by precipitation from ether and chromatography on silica, to give compound 88 (19.4 g, 69%).

TLC: Rf=0.37, silica gel, 6/1 v/v dichloromethane/ethyl ether

Preparation 76

1,6-Anhydro-4-O-p-methoxyphenyl-3-O-methyl-2-O-tosyl-β-D-glucopyranose (89)

Methyl iodide (54 ml, 954 mmol) and silver oxide (18.4 g, 79.5 mmol) are added to a solution of compound 88 (3.36 g, 7.95 mmol) in dry N,N-dimethylformamide (8 ml). After stirring for 16 h, the mixture is filtered (Celite), diluted with ethyl acetate (300 ml), washed with water (3×100 ml), dried (sodium sulphate), filtered, concentrated and purified by chromatography on silica to give the derivative 89 (3.23 g, 80%).

TLC: Rf 0.36, silica gel, 2/3 v/v cyclohexane/ethyl ether

Preparation 77

1,6-Anhydro-4-O-p-methoxyphenyl-3-O-methyl-2-O-benzoyl-β-D-mannopyranose (90)

Compound 89 (27.4 g, 62.7 mmol) is dissolved in N,N-dimethylformamide (315 ml). Tetrabutylammonium benzoate (341 g, 940 mmol) is then added and the solution is maintained at 150° C. for 3 h. After cooling to room temperature, the medium is diluted with ethyl acetate (300 ml), washed with water until neutral, dried and concentrated. The residue corresponding to compound 90 is used directly in the following step.

TLC: Rf=0.53, silica gel, 10/1 v/v dichloromethane/ethyl ether

Preparation 78

1,6-Anhydro-4-O-p-methoxyphenyl-3-O-methyl-β-D-mannopyranose (91)

Sodium methoxide (13.5 g, 250 mmol) is added to a solution of the above crude residue 90 in dichloromethane/methanol (540 ml, 1/1). After stirring for 1 h, the reaction medium is diluted with dichloromethane (500 ml) and then washed with aqueous 3% hydrochloric acid solution and water. After drying, filtration and concentration, the residue is purified on silica to give compound 91 (10.5 g, 59% over two steps).

TLC: Rf=0.29, silica gel, 1/1 v/v toluene/ethyl ether

Preparation 79

1,6-Anhydro-2-O-benzyl-4-O-p-methoxyphenyl-3-O-methyl-β-D-mannopyranose (92)

Benzyl bromide (6.2 ml, 51.9 mmol) is added to a solution of compound 91 (9.8 g, 34.6 mmol) in N,N-dimethylformamide (180 ml), followed, at 0° C., by addition of 95% sodium hydride (1.16 g, 48.4 mmol). After stirring for 16 h, methanol (3 ml) is added at 0° C. and the reaction mixture is diluted with ethyl acetate (200 ml), washed with water, dried, filtered and concentrated. The residue corresponding to compound 92 is used directly in the following step without purification. However, an analytical fraction is obtained after chromatography on silica.

$[\alpha]^{20}_D = -49$ (c=0.73, dichloromethane).

Preparation 80

1,6-Anhydro-2-O-benzyl-3-O-methyl-β-D-mannopyranose (93)

The above crude compound 92 is dissolved in a THF/water mixture (311 ml, 17/1) and ammonium cerium nitrate (76 g, 138 mmol) is then added at 0° C. After stirring for 30 minutes, the reaction mixture is diluted with dichloromethane (1 l) and then washed with aqueous 2% sodium hydrogen carbonate solution, and then with water. After drying, filtration and concentration, the residue is purified on silica to give compound 93 (6.63 g, 72% over two steps).

$[\alpha]^{20}_D = -68$ (c=1.02, dichloromethane).

The nonasaccharide 94 below is prepared from the monosaccharide 93 according to a reaction sequence similar to that carried out for the nonasaccharide 24 from the monosaccharide 3.

Preparation 81

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-anhydro-3-O-methyl-β-D-mannopyranose (95)

5% Pd/C (109 mg) is added to a solution of compound 94 (759 mg, 0.36 mmol) in a dichloromethane/t-butanol mixture (3.3 ml, 1/2). After stirring for 16 hours at 10 bar and at 55° C., the mixture is filtered and concentrated. Compound 95 is used in the following step without purification or characterization.

Preparation 82

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-anhydro-2-O-benzoyl-3-O-methyl-β-D-mannopyranose (96)

Benzoyl chloride (62 μl, 0.54 mmol) and dimethylaminopyridine (9 mg, 0.073 mmol) are added to a solution of compound 95 (726 mg, 0.36 mmol) in anhydrous pyridine (5.4 ml). After stirring for 2 hours at 60° C., the same amount of benzoyl chloride is added and, after 35 minutes, the solution is concentrated, the residue is taken up in dichloromethane, washed with aqueous 10% potassium hydrogen sulphate solution, aqueous 2% sodium hydrogen carbonate solution and then water. The organic phase is then dried over sodium sulphate, filtered and then concentrated.

SCHEME 18

Synthesis of the nonasaccharide 96

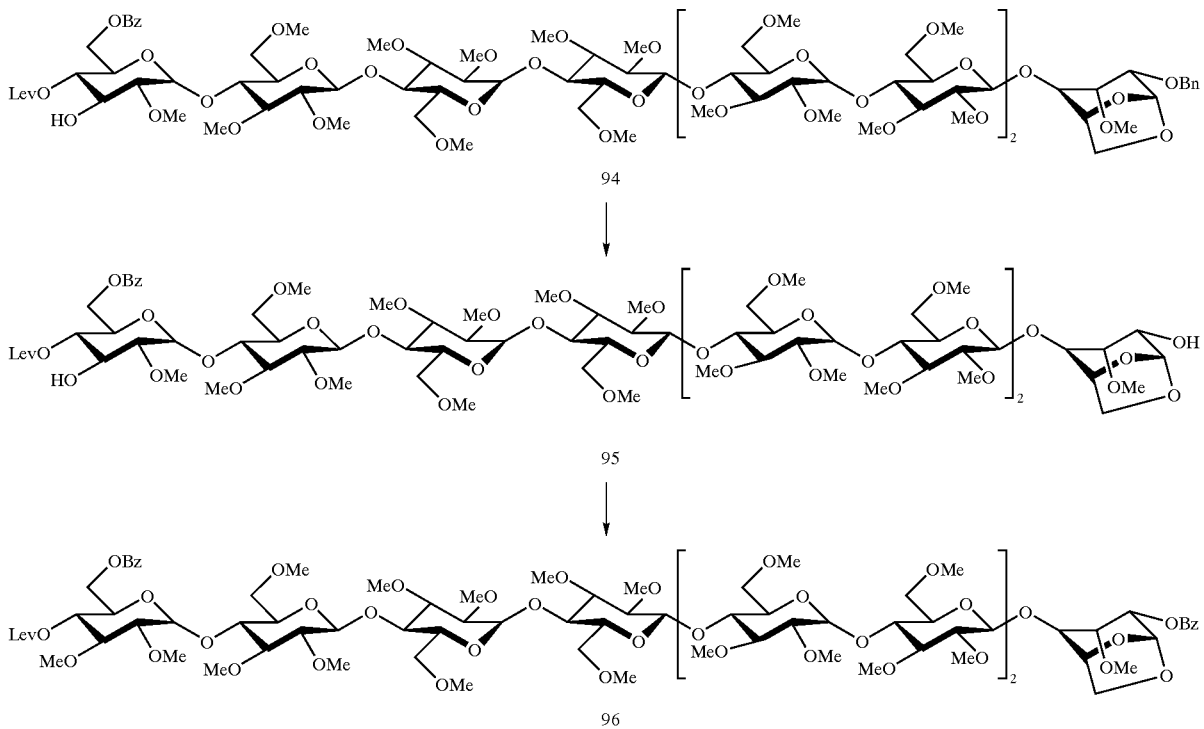

The residue is then purified on silica to give compound 96 (684 mg, 90% over two steps).

TLC: Rf=0.5, silica gel, 1/1 v/v toluene/acetone 5 hours. The mixture is then poured onto ice and, after extraction with ethyl ether, the organic phase is washed successively with 3% hydrochloric acid and water, dried and

SCHEME 19

Synthesis of the nonasaccharide 99

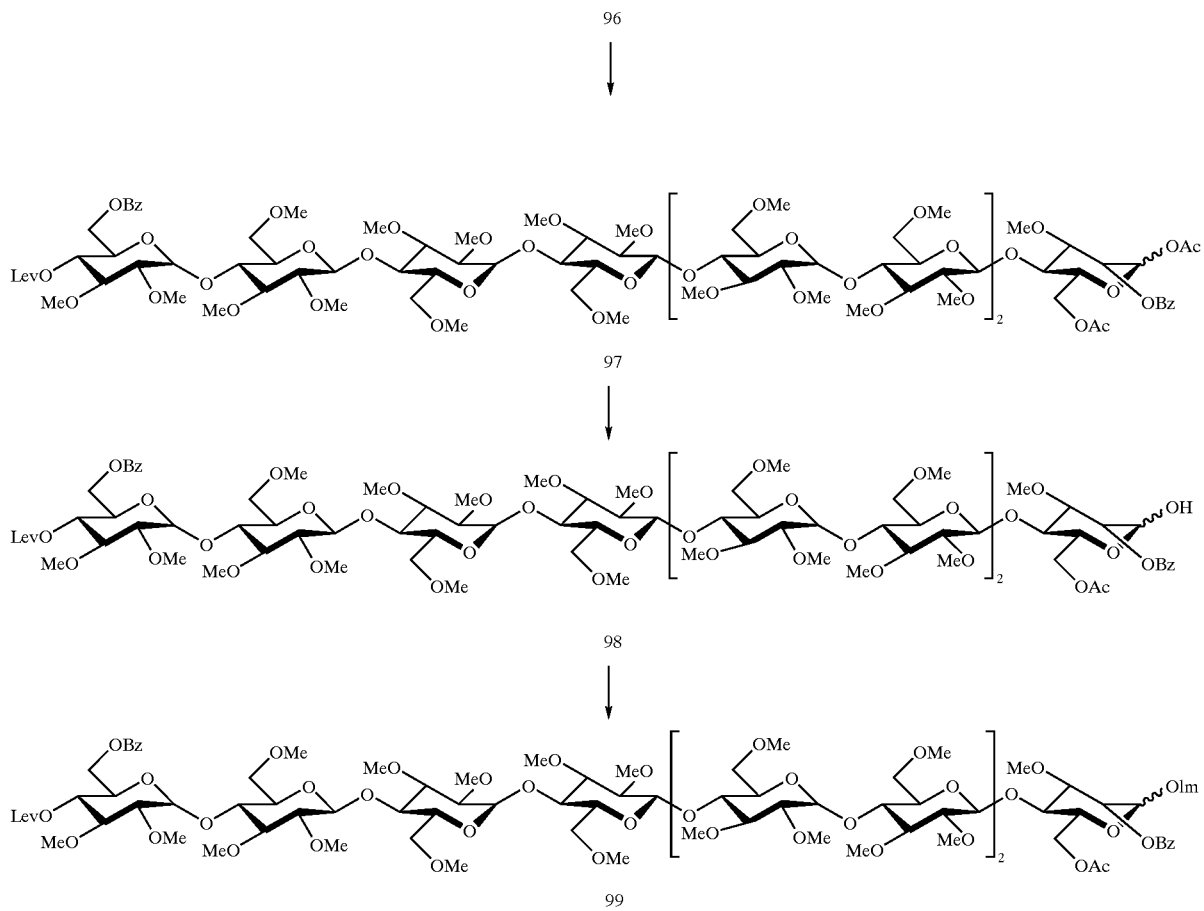

concentrated. After chromatography on a column of silica gel, compound 98 (241 mg) is obtained.

TLC: Rf=0.37, silica gel, 6/2/2 v/v/v toluene/ethyl acetate/ethanol

Preparation 83

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-1,6-di-O-acetyl-2-O-benzoyl-3-O-methyl-α,β-D-mannopyranose (97)

Compound 96 (657 mg, 0.31 mmol) is treated with a mixture of acetic anhydride (4.5 ml), acetic acid (100 μl) and trifluoroacetic acid (0.19 ml) as in Preparation 23. After chromatography on a column of silica gel, compound 97 (432 mg, 92%) is obtained.

TLC: Rf=0.53, silica gel, 1/1 v/v toluene/acetone

Preparation 84

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-6-O-acetyl-2-O-benzoyl-3-O-methyl-α,β-D-mannopyranose (98)

A solution of compound 97 (382 mg, 0.17 mmol) and of benzylamine (736 μl, 6.74 mmol) in THF (6 ml) is stirred for

Preparation 85

O-(6-O-Benzoyl-4-O-levulinoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-6-O-acetyl-2-O-benzoyl-3-O-methyl-α,β-D-mannopyranose trichloroacetimidate (99)

Trichloroacetonitrile (57 μl, 0.56 mmol) and caesium carbonate (58 mg) are added to a solution of compound 98 (241 mg) in dichloromethane (2.2 ml). After stirring for 1 hour, the mixture is filtered, concentrated and the residue is chromatographed on a column of silica gel to give the imidate 99 (221 mg, 56% over two steps).

TLC: Rf=0.19, silica gel, 3/2 v/v cyclohexane/acetone

EXAMPLE 1

Methyl O-(2,3,4,6-tetra-O-sulpho-α-D-glucopyranosyl)-(1→4)-O-(2,3,6-tri-O-sulpho-α-D-glucopyranosyl)-(1→4)-O-(2,3,6-tri-O-sulpho-β-D-glucopyranosyl)-(1→4)-O-(2,3-di-O-methyl-6-O-sulpho-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(2,3-di-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,3-di-O-methyl-α-L-idopyranosyluronic acid)-(1→4)-3-O-methyl-2,6-di-O-sulpho-α-D-glucopyranoside, sodium salt (I)

The hexadecasaccharide 46 (34 mg, 11 μmol) is dissolved in N,N-dimethylformamide (1 ml). Sulphur trioxide/triethylamine complex (180 mg, 0.89 mmol) is added and the mixture is stirred at 55° C. for 20 hours. Triethylamine/sulphur trioxide complex (5 mol/mol hydroxyl function) is added to a solution in N,N-dimethylformamide (5 mg/ml) of the compound to be sulphated. After 1 day at 55° C., the solution is placed at the top of a Sephadex® G-25 column (1.6×115 cm) and eluted with 0.2M sodium chloride. The fractions containing the product are concentrated and desalified using the same column eluted with water. Compound I (47 mg, 87%) is obtained, after freeze-drying, as a white powder. $[\alpha]^{20}_D$=+65 (c=1.0 water).

EXAMPLE 2

Methyl O-(2,3,4,6-tetra-O-sulpho-α-D-glucopyranosyl)-(1→4)-O-(2,3,6-tri-O-sulpho-α-D-glucopyranosyl)-(1→4)-O-(2,3,6-tri-O-sulpho-β-D-glucopyranosyl)-(1→4)-O-(2,3-di-O-methyl-6-O-sulpho-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(2,3-di-O-methyl-6-O-sulpho-α-D-glucopyranosyl)-(1→4)-O-(2,3-di-O-methyl-β-D-glucopyranosyluronic acid)-(1→4)-O-(6-O-methyl-2,3-di-O-sulpho-α-D-glucopyranosyl)-(1→4)-O-(2,3-di-O-methyl-α-L-idopyranosyluronic acid)-(1→4)-3,6-di-O-methyl-2-O-sulpho-α-D-glucopyranoside, sodium salt (II)

EXAMPLE 3

Methyl O-(2,3,4,6-tetra-O-sulpho-α-D-glucopyranosyl)-(1→4)-O-(2,3,6-tri-O-sulpho-α-D-glucopyranosyl)-(1→4)-O-(2,3,6-tri-O-sulpho-β-D-glucopyranosyl)-(1→4)-O-(2,3-di-O-methyl-6-O-sulpho-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(3-O-methyl-2,6-di-O-sulpho-α-D-mannopyranosyl)-(1→4)-O-(2,3-di-O-methyl-β-D-glucopyranosyluronic acid)-(1→4)-O-(6-O-methyl-2,3-di-O-sulpho-α-D-glucopyranosyl)-(1→4)-O-(2,3-di-O-methyl-α-L-idopyranosyluronic acid)-(1→4)-6-O-methyl-2,3-di-O-sulpho-α-D-glucopyranoside, sodium salt (III)

EXAMPLE 4

Methyl O-(2,3,4,6-tetra-O-sulpho-α-D-glucopyranosyl)-(1→4)-O-(2,3,6-tri-O-sulpho-α-D-glucopyranosyl)-(1→4)-O-(2,3,6-tri-O-sulpho-β-D-glucopyranosyl)-(1→4)-O-(2,3-di-O-methyl-6-O-sulpho-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(3-O-methyl-2,6-di-O-sulpho-α-D-mannopyranosyl)-(1→4)-O-(2,3-di-O-methyl-β-D-glucopyranosyluronic acid)-(1→4)-O-(6-O-methyl-2,3-di-O-sulpho-α-D-glucopyranosyl)-(1→4)-O-(2,3-di-O-methyl-α-L-idopyranosyluronic acid)-(1→4)-3,6-di-O-methyl-2-O-sulpho-α-D-glucopyranoside, sodium salt (IV)

EXAMPLE 5

Methyl O-(2,3,4,6-tetra-O-sulpho-α-D-glucopyranosyl)-(1→4)-O-(2,3,6-tri-O-sulpho-α-D-glucopyranosyl)-(1→4)-O-(2,3,6-tri-O-sulpho-β-D-glucopyranosyl)-(1→4)-O-(2,3-di-O-methyl-6-O-sulpho-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(2,3-di-O-methyl-6-O-sulpho-α-D-glucopyranosyl)-(1→4)-O-(2,3-di-O-methyl-β-D-glucopyranosyluronic acid)-(1→4)-O-(6-O-methyl-2,3-di-O-sulpho-α-D-glucopyranosyl)-(1→4)-O-(3-O-methyl-2-O-sulpho-α-L-idopyranosyluronic acid)-(1→4)-3,6-di-O-methyl-2-O-sulpho-α-D-glucopyranoside, sodium salt (V)

The compounds of Examples 2 to 5 were prepared in a similar manner by coupling an appropriate tetrasaccharide with the appropriate nonasaccharide and then coupling with the trisaccharide 41 or 43 (as described in Preparations 36 or 38), followed by the usual deprotection and sulphation reactions.

In the case of Example 2, the tetrasaccharide used is the one described in Preparation 55 (compound 62) and the nonasaccharide used is the one described in Preparation 25 (compound 27).

In the case of Example 3, the tetrasaccharide used is the one described in Preparation 74 (compound 86) and the nonasaccharide used is the one described in Preparation 85 (compound 99).

In the case of Example 4, the tetrasaccharide used is the one described in Preparation 55 (compound 62) and the nonasaccharide used is the one described in Preparation 85 (compound 99).

In the case of Example 5, the tetrasaccharide used is compound 68 and the nonasaccharide used is the one described in Preparation 25 (compound 27).

TABLE 1

$^1$H-NMR (D$_2$O, 4.80 ppm) δ of H-1 protons (ppm):

Unit 1=unit with reducing end

Unit 16=unit with non-reducing end

| Unit | EXAMPLE 2 | EXAMPLE 3 | EXAMPLE 4 | EXAMPLE 5 |
|---|---|---|---|---|
| 1 | 5.08 | 4.68 | 5.07 | 5.08 |
| 2 | 4.93 | 5.02 | 5.02 | 4.93 |
| 3 | 5.37 | 5.41 | 5.43 | 5.37 |
| 5 | 5.49 | 5.57 | 5.48 | 5.57 |
| 6 | 4.66 | 4.71 | 4.65 | 4.70 |
| 7, 9, 11 | 5.67 | 5.67 | 5.68 | 5.67 |
| 4, 8, 10, 12 | 4.39–4.49 | 4.39–4.49 | 4.37–4.47 | 4.39–4.39 |
| 13 | 5.61 | 5.61 | 5.60 | 5.61 |
| 14 | 4.8 | 4.94 | 4.93 | 4.93 |
| 15 | 5.59 | 5.59 | 5.59 | 5.59 |
| 16 | 5.69 | 5.69 | 5.69 | 5.68 |

TABLE II

"Negative ion electron spray ionization" (ESI) mass method

| EXAMPLE | formula | calculated | found |
|---|---|---|---|
| 2 | $C_{129}H_{224}O_{128}S_{15}$ | 4304.1 | 4304.5 |
| 3 | $C_{127}H_{220}O_{134}S_{17}$ | 4436.2 | 4436.2 |
| 4 | $C_{128}H_{222}O_{131}S_{16}$ | 4370.1 | 4370.4 |
| 5 | $C_{128}H_{222}O_{131}S_{16}$ | 4370.1 | 4370.5 |

What is claimed is:

1. A synthetic polysaccharide in acidic form and the pharmaceutically acceptable salts thereof, the anionic form of which corresponds to one of the formulae (I) to (V) below:

Active structures of the invention

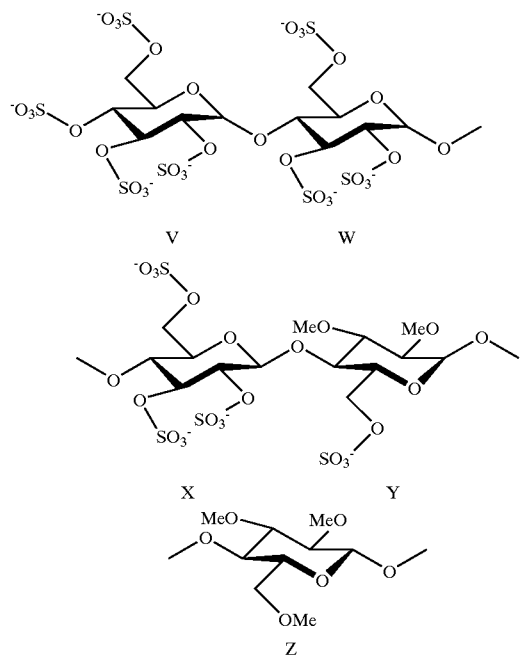

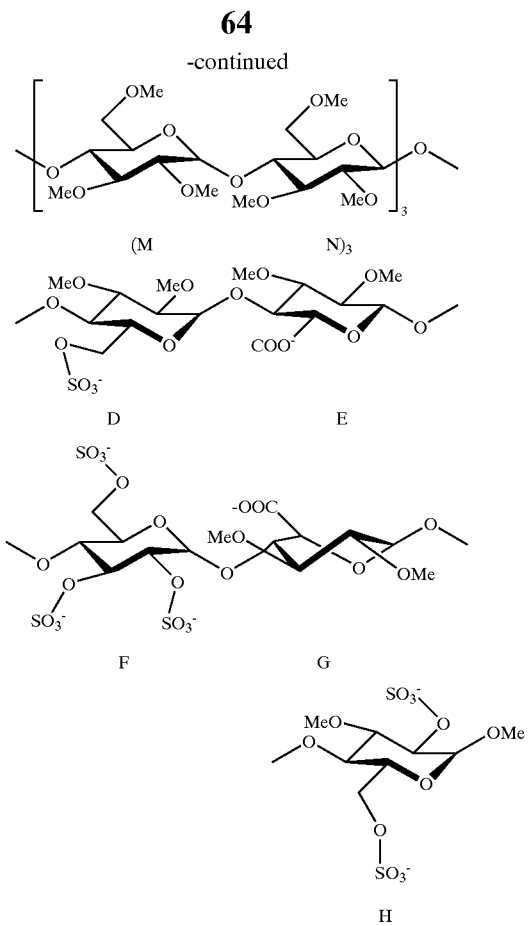

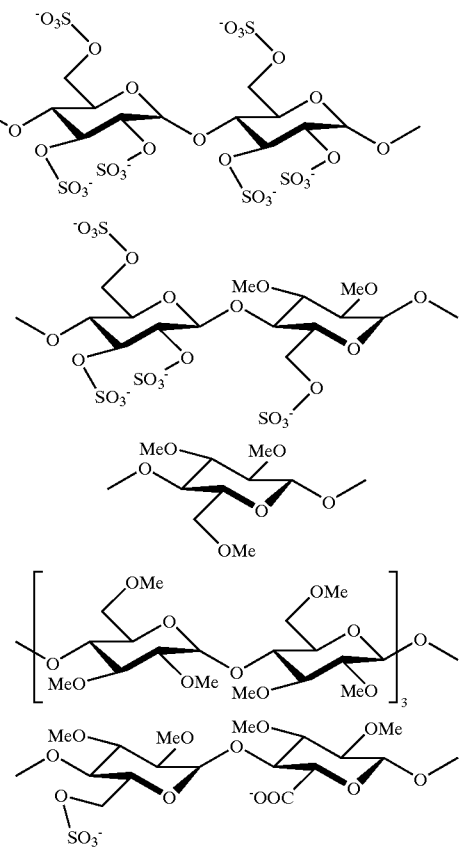

-continued
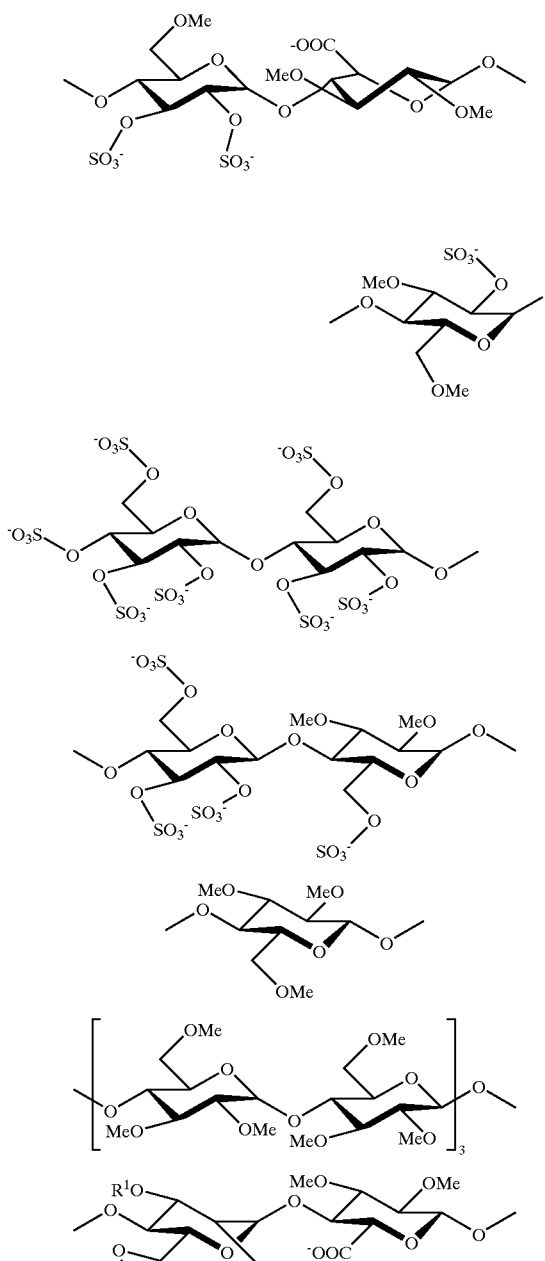
III
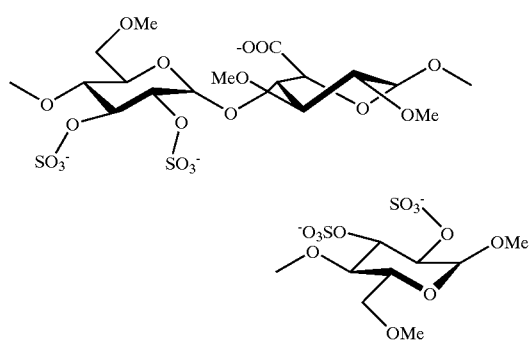
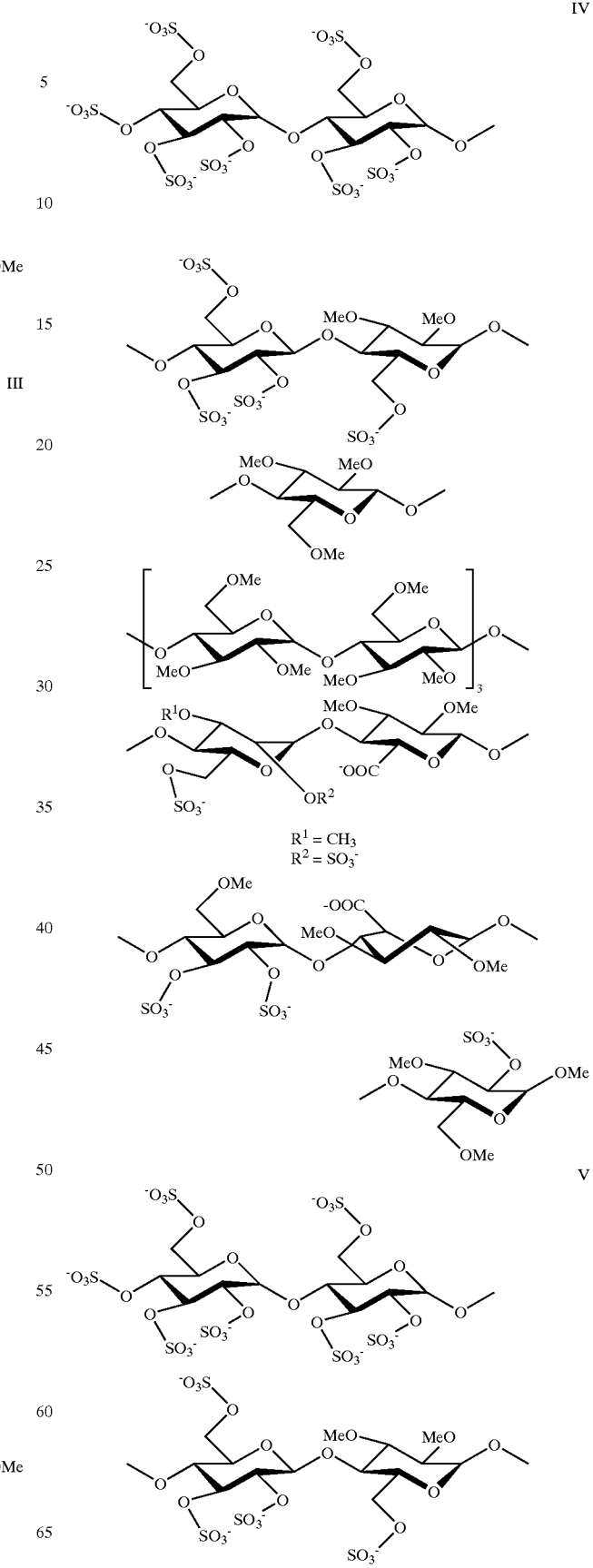
-continued
IV
V

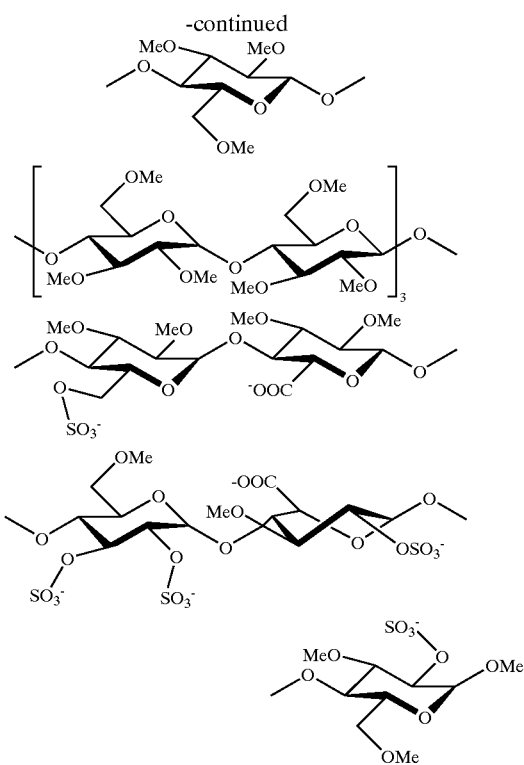

2. A polysacchiride according to claim 1, in the form of sodium or potassium salt.

3. A polysaccharide according to claim 2, of formula: methyl O-(2,3,4,6-tetra-O-sulpho-α-D-glucopyranosyl)-(1→4)-O-(2,3,6-tri-O-sulpho-α-D-glucopyranosyl)-(1→4)-O-(2,3,6-tri-O-sulpho-β-D-glucopyranosyl)-(1→4)-O-(2,3-di-O-methyl-6-O-sulpho-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-O-(2,3-di-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,3-di-O-methyl-α-L-idopyranosyluronic acid)-(1→4)-3-O-methyl-2,6-di-O-sulpho-α-D-glucopyranoside, sodium salt.

4. A pharmaceutical composition containing, as active principle, a polysaccharide according to claim 1 in the form of a salt with a pharmaceutically acceptable base or in acidic form, in combination or as a mixture with an inert, non-toxic, pharmaceutically acceptable excipient.

5. A pharmaceutical composition according to claim 4, in the form of a dosage unit containing from about 0.1 to about 100 mg of active principle.

6. A composition according to claim 5 in which each dosage unit contains from about 0.5 to about 50 mg of active principle.

7. A method for the inhibition or treatment of cardiovascular and cerebrovascular system disorders, thromboembolic disorders associated with arteriosclerosis and with diabetes, or thromboembolic disorders associated with rethrombosis after thrombolysis, with infarction, with dementia of ischaemic origin, with peripheral arterial diseases, with haemodialysis or with auricular fibrillation, or alternatively during the use of aorto-coronary bridge vascular prostheses which comprises administering to a patient in need of such treatment a therapeutically effective amount of a polysaccharide according to claim 1.

8. A pharmaceutical composition according to claim 4 wherein the polysaccharide is in the form of a sodium or potassium salt.

9. A pharmaceutical composition containing, as active principle, a polysaccharide according to claim 3.

10. A pharmaceutical composition according to claim 8 in the form of a dosage unit containing from about 0.1 to about 100 mg of active principle.

11. A pharmaceutical composition according to claim 9 in the form of a dosage unit containing from about 0.1 to about 100 mg of active principle.

12. A pharmaceutical composition according to claim 10 in which each dosage unit contains from about 0.5 to about 50 mg of active principle.

13. A pharmaceutical composition according to claim 11 in which each dosage unit contains from about 0.5 to about 50 mg of active principle.

14. A method for the inhibition or treatment of pathologies associated with a coagulation dysfunction which comprises administering to a patient in need of such treatment a therapeutically effective amount of a polysaccharide according to claim 1.

15. A method according to claim 14 wherein the polysaccharide is in the form of a sodium or potassium salt.

16. A method for the inhibition or treatment of pathologies associated with a coagulation dysfunction which comprises administering to a patient in need of such treatment a therapeutically effective amount of a polysaccharide according to claim 3.

17. A method according to claim 7 wherein the polysaccharide is in the form of a sodium or potassium salt.

18. A method for the inhibition or treatment of cardiovascular and cerebrovascular system disorders, thromboembolic disorders associated with arteriosclerosis and with diabetes, or thromboembolic disorders associated with rethrombosis after thrombolysis, with infarction, with dementia of ischaemic origin, with peripheral arterial diseases, with haemodialysis or with auricular fibrillation, or alternatively during the use of aorto-coronary bridge vascular prostheses which comprises administering to a patient in need of such treatment a therapeutically effective amount of a polysaccharide according to claim 3.

19. A method according to claim 7 for the inhibition or treatment of thromboembolic diseases.

20. A method according to claim 19 for the inhibition or treatment of thromboembolic diseases.

21. A method according to claim 18 for the inhibition or treatment of thromboembolic diseases.

22. A method according to claim 19 for the inhibition or treatment of unstable angina, strokes, or restenosis after angioplasty, endarterectomy or the installation of endovascular prostheses.

23. A method according to claim 20 for the inhibition or treatment of unstable angina, strokes, or restenosis after angioplasty, endarterectomy or the installation of endovascular prostheses.

24. A method according to claim 21 for the inhibition or treatment of unstable angina, strokes, or restenosis after angioplasty, endarterectomy or the installation of endovascular prostheses.

* * * * *